(12) United States Patent
Turecek et al.

(10) Patent No.: US 9,265,791 B2
(45) Date of Patent: *Feb. 23, 2016

(54) RESORPTION ENHANCERS AS ADDITIVES TO IMPROVE THE ORAL FORMULATION OF LOW MOLECULAR WEIGHT HEPARINS

(71) Applicants: BAXTER INTERNATIONAL INC., Deerfield, IL (US); BAXTER HEALTHCARE S.A., Glattpark (Opfikon) (CH)

(72) Inventors: Peter Turecek, Klosterneuburg (AT); Susanne Vejda, Vienna (AT)

(73) Assignees: Baxalta GmbH, Zürich (CH); Baxalta Incorporated, Bannockburn, IL (US)

(*) Notice: Subject to any disclaimer, the term of this patent is extended or adjusted under 35 U.S.C. 154(b) by 11 days.

This patent is subject to a terminal disclaimer.

(21) Appl. No.: 14/160,235

(22) Filed: Jan. 21, 2014

(65) Prior Publication Data

US 2014/0271608 A1   Sep. 18, 2014

Related U.S. Application Data

(60) Provisional application No. 61/778,113, filed on Mar. 12, 2013.

(51) Int. Cl.

| | | |
|---|---|---|
| A61K 31/727 | (2006.01) | |
| A61K 31/722 | (2006.01) | |
| A61K 38/48 | (2006.01) | |
| A61K 47/36 | (2006.01) | |
| A61K 47/28 | (2006.01) | |
| A61K 47/46 | (2006.01) | |
| A61K 45/06 | (2006.01) | |
| A61K 47/12 | (2006.01) | |

(52) U.S. Cl.
CPC .............. *A61K 31/727* (2013.01); *A61K 31/722* (2013.01); *A61K 38/4873* (2013.01); *A61K 45/06* (2013.01); *A61K 47/12* (2013.01); *A61K 47/28* (2013.01); *A61K 47/36* (2013.01); *A61K 47/46* (2013.01)

(58) Field of Classification Search
None
See application file for complete search history.

(56) References Cited

U.S. PATENT DOCUMENTS

| 8,114,842 B1 | 2/2012 | Sung et al. |
|---|---|---|
| 2005/0282775 A1 | 12/2005 | Kennedy |
| 2013/0035288 A1 | 2/2013 | Turecek et al. |

FOREIGN PATENT DOCUMENTS

| CN | 1328062 | 12/2001 |
|---|---|---|
| CN | 1344565 | 4/2002 |
| CN | 1320002 | 1/2006 |
| EP | 251134 | 1/1988 |
| JP | 7215990 | 8/1995 |
| JP | 2002262788 | 9/2002 |
| JP | 3371124 | 1/2003 |
| WO | WO9815292 | 4/1998 |
| WO | WO2008090631 | 7/2008 |

OTHER PUBLICATIONS

Ross et al., "Gastrointestinal Absorption of Heparin by Lipidization or Coadministration with Penetration Enhancers", Current Drug Delivery 2005, vol. 2, pp. 277-287.*
Paliwal et al., "Chitosan nanoconstructs for improved oral delivery of low molecular weight heparin: In vitro and in vivo evaluation", International Journal of Pharmaceutics 2012, vol. 422, pp. 179-184.*
Giles, et al., "A canine model of hemophilic (factor VIII:C deficiency) bleeding", Blood, vol. 60, No. 3, pp. 727-730, 1982.
Bates, et al., "The New Heparins," Coron. Artery Dis. 2(2-3):65-74 (1998).
Guggi, et al., "Improved paracellular uptake by the combination of different types of permeation enhancers," Int J Pharm., 2005, 288(1):141-50.
Bishop, et al., "Recombinant Biologics for Treatment of Bleeding Disorders," Nat. Rev. Drug Discov. 2.(8):684-94, 2004.
Bourin, et al., "Glycosaminoglycans and the Regulation of Blood Coagulation," Biochem J. 289(Pt2):313-30, 1993.
Broze, "The Role of Tissue Factor Pathway Inhibitor in a Revised Coagulation Cascade," Semin. Haematol. 29(3): 159-69, 1992.
Brummel, et al., "Factor Viia Replacement Therapy in Factor VII Deficiency," J. T'hromb. Haemost. 6(10): 1735-44, 2004.
Church, et al., "Antithrombin Activity of Fucoidan. The Interaction of Fucoidan With Heparin Cofactor II, Antithrombin III, and Thrombin," J. Bioi. Chem. 264(6):3618-23, 1989.
Colliec, et al., "Anticoagulant Properties of a Fucoidan Fraction," Thrombosis Research, 64: 143-154, 1991.
Davie, et al., "The Coagulation Cascade: Initiation, Maintenance, and Regulation," Biochemistry 30(43): 10363-70, 1991.
Gailani et al., "Factor XI Activation in a Revised Model of Blood Coagulation" Science. (1991) vol. 253, No. 5022 pp. 909-912.
Giedrojc, et al., "Comparative Study on the In Vitro and In Vivo Activities of Heparinoids Derivative Investigated on the Animal Model," J. Cardiovasc. Pharmacol. 34(3):340-5 (1999).
Goodman-Gilman, "The Pharmacological Basis of Therapeutics" editors Joel G. Hardman and Lee E. Limbard; published by the McGraw-Hill Companies Inc., (2001) pp. 54-56.

(Continued)

*Primary Examiner* — Renee Claytor
*Assistant Examiner* — Michelle F Paguio Frising
(74) *Attorney, Agent, or Firm* — Khih K. Chin; Bret E. Field; Bozicevic, Field & Francis LLP

(57) ABSTRACT

Aspects of the invention include methods for treating or preventing a thromboembolic disease in a subject. In practicing methods according to certain embodiments, an amount of a low molecular weight heparin (LMWH) and a synergistically effective combination of two or more gastrointestinal epithelial barrier permeation enhancers is orally administered to a subject in a manner sufficient to treat the thromboembolic disease in the subject. Compositions and kits for practicing methods of the invention are also described.

13 Claims, 14 Drawing Sheets

(56) References Cited

OTHER PUBLICATIONS

Grabovac, et al. "Improvement of the intestinal membrane permeability of low molecular weight heparin by complexation with stem bromelain" International Journal of Pharmaceutics 326; pp. 153-159 (2006).
Hirsh, et al., "New Anticoagulants," Blood W(2):453-63 (2005).
Johnson, et al. "Discovery of tight junction modulators: significance for drug development and delivery," Drug Discovery Today vol. 13, Nos. 5/6 (Mar. 2008).
Johnson, et al., "Novel Anticoagulants Based on Inhibition of the Factor ViialTissue Factor Pathway," Coron. Artery Dis. 2(2-3):83-7 (1998).
Kleesiek, et al., "The 536C—>T Transition in the Human Tissue Factor Pathway Inhibitor (TFPJ) Gene Is Statistically Associated With a Higher Risk for Venous Thrombosis," Thromb. Haemost. 82(1):1-5 (1999).
Kleim et al., "Successful renal transplantation in severe von Willebrand's disease" Nephrology Dialysis Transplantation vol. 9, p. 837-838 (1994).
Lee, "Von Willebrand Disease, Hemophilia A and B, and Other Factor Deficiencies," Int. Anesthesiol. Clin. 42 (3):59-76 (2004).
MacGregor, et al., "Metabolism of sodium pentosan polysulphate in man measured by a new competitive binding assay for sulphated polysaccharides—comparison with effects upon anticoagulant activity, lipolysis and platelet alpha-granule proteins," Thromb Haemost. Jun. 24, 1985;53(3):411-4.
Mann, "Thrombin: can't live without it; probably die from it." Chest. Sep. 2003;124(3 Suppl):1S-3S.
Mann, "Thrombin Formation," Chest 124(3 Suppl):4S-10S (2003).
McAuliffe, et al. "Carbohydrate drugs—an ongoing challenge," Chem.Indus. Magazine 2:170-4 (1997).
Millet, et al. "Antithrombotic and Anticoagulant Activities of a Low Molecular Weight Fucoidan by the Subcutaneous Route," Thromb. Haemost. 81:391-5 (1999).
Mourao, "Use of Sulfated Fucans as Anticoagulant and Antithombotic Agents: Future Perspectives," Curr Pharma Des 10:967-981 (2004).
Nordfang, et al. "Inhibition of extrinsic pathway inhibitor shortens the coagulation time of normal plasma and of hemophilia plasma." Thromb Haemost Oct. 1, 1991;66(4):464-7.
Novotny, et al. "Purification and properties of heparin-releasable lipoprotein-associated coagulation inhibitor." Blood. Jul. 15, 1991;78(2):394-400.
Orgueria, et al. "Modular synthesis of heparin oligosaccharides." Chem Eur J. Jan. 3, 2003;9(1):140-69.
Raimondi, et al. "Bile acids modulate tight junction structure and barrier function of Caco-2 monolayers via EGFR activation." Am J Physiol Gastrointest Liver Physiol. Apr. 2008;294(4):G906-13. doi: 10.1152/ajpgi.00043.2007. Epub Jan. 31, 2008.
Rapaport, et al., "The tissue factor pathway: how it has become a 'prima ballerina'" Thromb Haemost. Jul. 1995;74(1):7-17.
Roberts, et al. "Current concepts of hemostasis: implications for therapy." Anesthesiology. Mar. 2004;100(3):722-30.
Schipper, et al. "Chitosans as absorption enhancers for poorly absorbable drugs. 1: Influence of molecular weight and degree of acetylation on drug transport across human intestinal epithelial (Caco-2) cells." Pharm Res. Nov. 1996;13(11):1686-92.
Fogarty, Patrick F., "Biological rationale for new drugs in the bleeding disorders pipeline", Hematology Am Soc Hematol Educ Program, 2011; 397-404.
Irhimeh et al., "Pilot clinical study to evaluate the anticoagulant activity of fucoidan", Blood Coagulation and Fibrinolysis, 2009, vol. 20, No. 7, pp. 607-610.
National Research Council, "Guide for the Care and Use of Laboratory Animals", by Institute of Laboratory Animal Resources, National Research Council, Nat. Acad. Press, 1996.
Pipe, Steven W., "Hemophilia: new protein therapeutics", Hematology Am Soc Hematol Educ Program, 2010:203-9.
Schaub, Robert G., "Recent advances in the development of coagulation factors and procoagulants for the treatment of hemophilia", Biochem Pharmacol. 2011;15;82(2):91-8.
Sinay, Pierre, "Sugars Slide Into Heparin Activity," Nature, 1999;398(6726):377-8.
Springer, et al., "Isolation of anticoagulant fractions from crude fucoidin", Proc Soc Exp Biol Med. 1957;94(2):404-9.
Thanou, et al., "Mono-N-carboxymethyl chitosan (MCC), a polyampholytic chitosan derivative, enhances the intestinal absorption of low molecular weight heparin across intestinal epithelia in vitro and in vivo", J Pharm Sci. 2001;90(1):38-46.
Toida ei al. "Structure and Bioactivity of Sulfated Polysaccarides", Glycoscience and Glycotechnology, 2003;15(81):29-46.
Van'T Veer, et al., "Regulation of Tissue Factor Initiated Thrombin Generation by the Stoichiometric Inhibitors Tissue Factor PATHWA Y Inhibitor, Antithrombin-III, and Heparin Cofactor-II", Journal of Biological Chemistry, American Society of Biolochemical Biologists, Birmingham, 1997;US, 272(7):4367-4377.
Vicente, et al., "Unbalanced Effects of 1-23 Dermation Sulfates With Different Sulfation Patterns on Coagulation, Thrombosis and Bleeding," Thromb Haenos, 2001 86(5): 121 5-1220.
Wang, et al., "N-Desulfated Non-Anticoagulant Heparin Inhibits Leukocyte Adhesion and Transmigration In Vitro and Attenuates Acute Peritonitis and Ischemia and Reperfusion Injury In Vivo," Inflamm. Res., 2002;51(9):435-43.
Welsch, et al., "Effect of lipoprotein-associated coagulation inhibitor (LACI) on thromboplastin-induced coagulation of normal and hemophiliac plasmas", Thromb. Res., 1991;64(2):213-22.
Williams, et al., "Comparative Effects of Heparin and the Sulfatoid GMI474 on Coagulation parameters in Plasma and Blood From Various Species," Gen. Pharmacol., 1998; 30(3):337-41.
Wuilllemin, et al., "Thrombin-mediated activation of endogenous factor XI in plasma in the presence of physiological glycosaminoglycans occurs only with high concentrations of thrombin", Br J Haematol.,1996;92(2):466-72.
Anderson, et al., "Anticoagulant properties of heparin fractionated by affinity chromatography on matrix-bound antithrombin-3 and by gel-filtration", Thromb. Res., 9, 575-580, 1976.
Pijnappels, et al., "Evaluation of the cuticle bleeding time in canine haemophilia A", Thromb Haemost., 28;55(1):70-3, 1986.
Bernkop-Schnurch, et al., "Chemically modified chitosans as enzyme inhibitors", Adv Drug Deily Rev., 5;52(2):127-37, 2001.
Lanke, et al., "Oral delivery of low molecular weight heparin microspheres prepared using biodegradable polymer matrix system", J Microencapsul.,26(6):493-500, 2009.
Whitehead, et al., "Mechanistic analysis of chemical permeation enhancers for oral drug delivery", Pharm Res.,25(6):1412-9, 2008.
Broze, et al., "A Tail Vein Bleeding Time Model and Delayed Bleeding in Hemophiliac Mice", Thromb Haemost., 85:747-8, 2001.
Scallan, et al., "Sustained phenotypic correction of canine hemophilia A using an adeno-associated viral vector", Blood, vol. 102, No. 6, pp. 2031-2037, 2003.

* cited by examiner

RESORPTION ENHANCERS AS ADDITIVES TO IMPROVE THE ORAL FORMULATION OF LOW MOLECULAR WEIGHT HEPARINS

CROSS REFERENCE TO RELATED APPLICATIONS

Pursuant to 35 U.S.C. §119 (e), this application claims priority to the filing date of the U.S. Provisional Patent Application Ser. No. 61/778,113, filed Mar. 12, 2013; the disclosure of which is herein incorporated by reference.

INTRODUCTION

Thrombosis is the production of a mass of blood constituents within the circulatory system and may occlude arterial or venous blood vessels. Arterial thrombosis occurs when blood coagulates at the site of platelet deposition on an arterial wall. Diseases associated with arterial thrombosis include coronary artery disease, peripheral vascular disease and stroke. Venous thrombosis is typically the result of venous stasis during and following operation or prolonged inactivity. Venous thrombosis may lead to deep vein thrombosis and pulmonary embolism.

Anticoagulants can be used to treat or prevent thromboembolic diseases. Prevention and treatment of arterial and venous thrombosis can include treatment with low molecular weight heparins which act as anti-thrombin agents or antagonists of coagulation factors such as Factor Xa.

SUMMARY

Aspects of the invention include methods for treating or preventing a thromboembolic disease in a subject. In practicing methods according to certain embodiments, an amount of a low molecular weight heparin (LMWH) and a synergistically effective combination of two or more gastrointestinal epithelial barrier permeation enhancers is orally administered to a subject in a manner sufficient to treat the thromboembolic disease in the subject. Compositions and kits for practicing methods of the invention are also described.

In embodiments of the present invention, the combination of two or more gastrointestinal epithelial barrier permeation enhancers is a synergistically effective combination of gastrointestinal epithelial barrier permeation enhancers. As described in greater detail below, the phrase "synergistically effective" refers to a combination of two or more gastrointestinal epithelial barrier permeation enhancers in an amount (e.g., ratio) which produces an effect (i.e., enhances gastrointestinal epithelial barrier permeation of low molecular weight heparin) which is greater than would be achieved by the sum of the individual gastrointestinal epithetial barrier permeation enhancers. For example, the combination of two or more gastrointestinal epithelial barrier permeation enhancers produces an effect that is 1.5-fold or greater than would be achieved by the sum of the individual gastrointestinal epithelial barrier permeation enhancers, such as 2-fold or greater, such as 3-fold or greater, such as 4-fold or greater, such as 5-fold or greater, such as 10-fold or greater and including 25-fold or greater than would achieved with the sum of the individual gastrointestinal epithelial barrier permeation enhancers.

In some embodiments, one or more of the gastrointestinal epithelial barrier permeation enhancers is a tight junction modulator. For example, tight junction modulators provided by the invention may include, but are not limited to proteases, bile acids, polysaccharides, fatty acids and salts thereof and any combination thereof. For example, the tight junction modulator may be a bile acid, such as for instance deoxycholate. In other instances, the tight junction modulator may be a protease, such as bromelain, trypsin, papain or an enzymatic component thereof. In yet other instances, the tight junction modulator may be a polysaccharide, such as chitosan. In still other instances, the tight junction modulator may be a fatty acid or a fatty acid salt, such as sodium caprate.

In certain embodiments, methods include orally administering to a subject low molecular weight heparin with a synergistically effective combination of bromelain and chitosan. In these embodiments, the combination of bromelain and chitosan enhances gastrointestinal epithelial barrier permeation of the low molecular weight heparin by 1.5-fold or greater, 2-fold or greater than would be achieved by the sum of chitosan and bromelain individually, such as 3-fold or greater, such as 4-fold or greater, such as 5-fold or greater, such as 10-fold or greater and including 25-fold or greater than would achieved with the sum of chitosan and bromelain individually. In some instances, the magnitude of increase is 1000-fold or less, such as 750-fold or less, including 500-fold or less, e.g., 250-fold or less, including 100-fold or less. In certain instances, the chitosan is unmodified chitosan. As described in greater detail below, the term "unmodified chitosan" is used in its conventional sense to refer to chitosan which has not been chemically derivatized or modified in any way to enhance or otherwise change chemical structure. As such, unmodified chitosan refers to the linear polysaccharide composed of randomly distributed $\beta$-(1-4)-linked D-glucosamine and N-acetyl-D-glucosamine saccharide units that has not been modified to include any foreign moieties, such as by sulfation, acetylation, glycosylation, phosphorylation, polymer conjugation (including with polyethylene glycol). For example, unmodified chitosan exclude chitosans which have been thiolated (such as, for example, chitosan-thio-butylamidine) to provide sulfhydryl groups or methylated (such as, for example, N-trimethyl-chitosan) to provide methyl groups fixed to the surface of the polysaccharide structure.

In some embodiments, the present invention provides a method for orally administering a composition having an amount of a low molecular weight heparin with a synergistically effective combination of two or more gastrointestinal epithelial barrier permeation enhancer to a subject, where the low molecular weight heparin is Bemiparin, Certoparin, Dalteparin, Enoxaparin, Nadroparin, Parnaparin, Reviparin and Tinzaparin and combinations thereof.

In certain embodiments, methods include treating or preventing a thromboembolic disease in a subject, where the thromboembolic disease is associated with myocardial infarction, deep vein thrombosis following surgery, transient ischemic attack, coronary artery bypass graft, peripheral vascular disease, stroke percutaneous transluminal coronary angioplasty, acute promyelocytic leukemia, diabetes, multiple myelomas, septic shock, purpura fulminanas, adult respiratory distress syndrome, angina, insertion and the presence of aortic valve or vascular prosthesis, cardiac catherization, transluminal endoplasty, heart valve replacement.

In certain embodiments, compositions of interest demonstrate enhanced permeation, for example, when determined by resorption studies in CaCo-2 cell models as compared to compositions in the absence of gastrointestinal epithelial permeation enhancers, compositions having only a single gastrointestinal epithelial permeation enhancer or compositions having two non-synergistically effective gastrointestinal epithelial permeation enhancers.

RELEVANT DEFINITIONS

Figure 1:
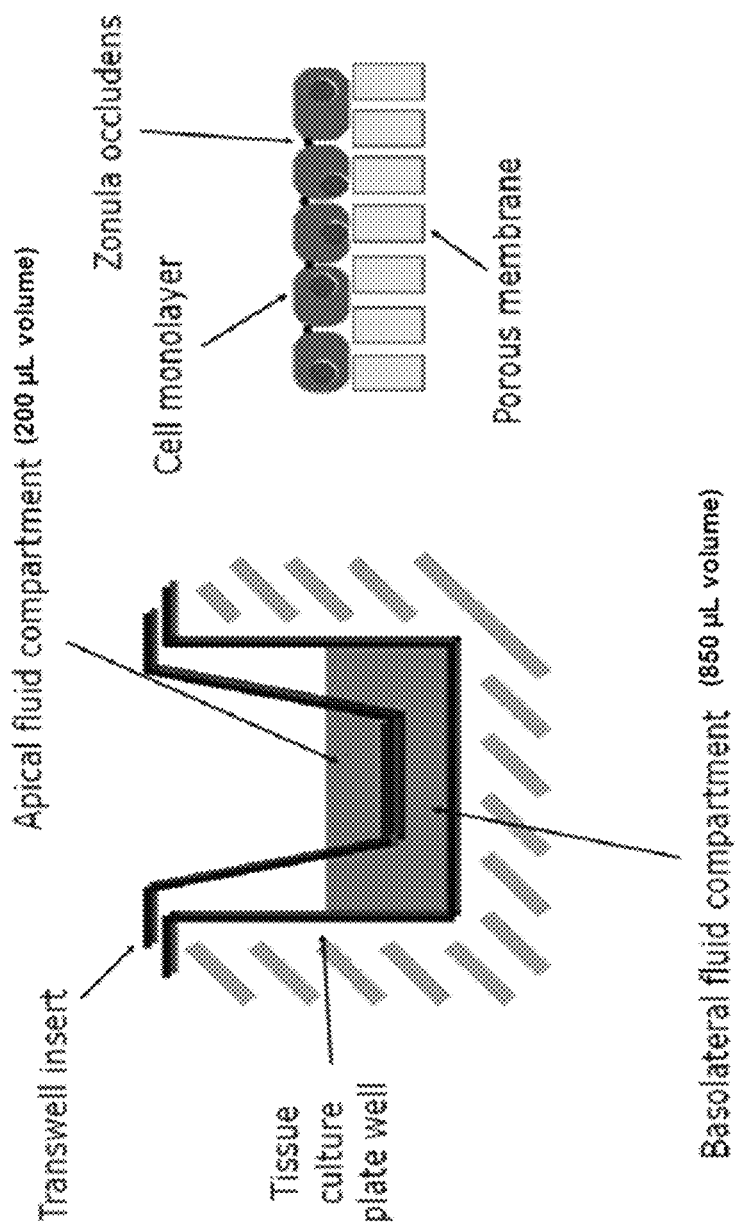
FIG. 1 shows the experimental setup for CaCo2 bioavailability screening to determine the % resorption of low molecular weight heparins.

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to a "LMWH" may include a mixture of two or more LMWH, as desired.

A "low molecular weight heparin" (LMWH) as used herein refers to the class of short chain sulfated polysaccharides (SP) that exhibit anticoagulant activity in any of the various clotting assays described herein to treat conditions that feature undesired thrombosis, as well as for prophylaxis for high risks of undesired thrombosis. As described in greater detail below, the term undesired thrombosis refers to the formation of a clot within a blood vessel which can interfere with the blood supply to tissues and can cause complications, such as for example deep vein thrombosis, pulmonary embolisms, heart attacks or strokes (i.e., cause a thromboembolic disease). Low molecular weight heparin may be natural sulfated polysaccharides, such as those fractionated and depolymerized from a biological source of unfractionated heparin or synthetic sulfated polysaccharides, where the sulfated polysaccharide is partially or wholly produced by synthetic methods (e.g., chemical synthesis). One measure of activity is to compare the clotting time demonstrated by a low molecular weight heparin with the anticoagulant activity displayed by unfractionated heparin. For example, low molecular weight heparins of interest exhibit anticoagulant and anti-thrombotic activity in the dilute prothrombin time (dPT) or activated partial thromboplastin time (aPTT) clotting assay that is at least equal to or greater than the molar anticoagulant and anti-thrombotic activity of unfractionated heparin (MW range 5,000 to 40,000; mean 18,000 daltons).

Low molecular weight heparins of interest are short chain sulfated polysaccharides which may have a range in molecular weight from 2000 daltons to 12,000 daltons, such as for example, from 2500 daltons to 10,000 daltons, such as from 3000 daltons to 9500 daltons, such as from 3500 daltons to 9000 daltons, including 4000 daltons to 8500 daltons. Low molecular weight heparins may range in average molecular weight from 2000 daltons to 10,000 daltons, such as from 2500 daltons to 9000 daltons, such as from 3000 daltons to 8500 daltons, including 4000 daltons to 8000 daltons.

In some instances, low molecular weight heparins of interest may include, but are not limited to Ardeparin, Bemiparin, Bioparin, Certoparin, Dalteparin, Enoxaparin, Miniparin, Nadroparin, Parnaparin, Reviparin, Sandoparin and Tinzaparin and combinations thereof.

Low molecular weight heparins with a synergistically effective combination of two or more gastrointestinal epithelial barrier permeation enhancers may be used in methods of the invention for improving hemostasis, in treating thromboembolic diseases, such as those associated with arterial and venous thrombosis, manifesting as a vascular thrombosis or pulmonary embolism, in particular when enhanced resorption by the gastrointestinal system is necessary or desired. The ability of low molecular weight heparins to inhibit thrombosis and reduce clotting may be determined using various in vitro clotting assays (e.g., thrombin generation and thromboelastography (TEG) or calibrated automated thrombography (CAT) assays) and in vivo bleeding models (e.g. tail snip, transverse cut, whole blood clotting time, or cuticle bleeding time determination in hemophilic mice or dogs). See, e.g., PDR Staff. Physicians' Desk Reference. 2004, Anderson et al. (1976) Thromb. Res. 9:575-580; Nordfang et al. (1991) Thromb Haemost. 66:464-467; Welsch et al. (1991) Thrombosis Research 64:213-222; Broze et al. (2001) Thromb Haemost 85:747-748; Scallan et al. (2003) Blood. 102:2031-2037; Pijnappels et al. (1986) Thromb. Haemost. 55:70-73; and Giles et al. (1982) Blood 60:727-730, and the examples herein.

The term "polysaccharide," as used herein, refers to a polymer containing two or more covalently linked saccharide residues. Saccharide residues may be linked for example by glycosidic, ester, amide, or oxime linking moieties. The average molecular weight of polysaccharides may vary widely, such as for example ranging from 2000 daltons to 12,000 daltons, such as for example, from 2500 daltons to 10,000 daltons, such as from 3000 daltons to 9500 daltons, such as from 3500 daltons to 9000 daltons, including 4000 daltons to 8500 daltons. Polysaccharides may be straight chained (i.e., linear) or branched or may contain discrete regions of linear and branched portions. Polysaccharides may also be fragments of polysaccharides generated by degradation (e.g., hydrolysis) of larger polysaccharides. Degradation can be achieved by any convenient protocol including treatment of polysaccharides with acid, base, heat, oxidants or enzymes to yield fragmented polysaccharides. Polysaccharides may be chemically altered and may be modified, including but not limited to, sulfation, polysulfation, esterification, and methylation.

Molecular weight, as discussed herein, can be expressed as either a number average molecular weight or a weight average molecular weight. Unless otherwise indicated, all references to molecular weight herein refer to the weight average molecular weight. Both molecular weight determinations, number average and weight average, can be measured using for example, gel permeation chromatography or other liquid chromatography techniques.

The term "derived from" is used herein to identify the original source of a molecule but is not meant to limit the method by which the molecule is made which can be, for example, by chemical synthesis or recombinant methodologies.

The terms "variant," "analog" and "mutein" refer to biologically active derivatives of a reference molecule, that retain desired activity, such as anticoagulant activity in the treatment of a thromboembolic disease. The terms "variant" and "analog" in reference to a polypeptide (e.g., clotting factor) refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. The amino acid sequences of such analogs will have a high degree of sequence homology to the reference sequence, e.g., amino acid sequence homology of 50% or more, such as 60% or more, such as 70% or more, such as 80% or more, such as 90% or more, such as 95% or more, including 99% or more (and in some instances being 100% or less) when the two sequences are aligned. In some instances, analogs will include the same number of amino acids but will include substitutions. The term "mutein" further includes polypeptides having one or more amino acid-like molecules including but not limited to compounds contain only amino and/or imino molecules, polypeptides containing one or more analogs of an amino acid (including, for example, synthetic non-naturally occurring amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). In embodiments of the invention, analogs and muteins have at least the same clotting activity as the native molecule.

As discussed above, analogs may include substitutions that are conservative, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are in some instances classified as aromatic amino acids. For example, an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact.

By "derivative" is meant any suitable modification of the reference molecule of interest or of an analog thereof, such as sulfation, acetylation, glycosylation, phosphorylation, polymer conjugation (such as with polyethylene glycol), or other addition of foreign moieties, so long as the desired biological activity (e.g., reduced thrombotic activity) of the reference molecule is retained. For example, low molecular weight heparin polysaccharides may be derivatized with one or more organic or inorganic groups. Examples include but are not limited to polysaccharides substituted in at least one hydroxyl group with another moiety (e.g., a sulfate, carboxyl, phosphate, amino, nitrile, halo, silyl, amido, acyl, aliphatic, aromatic, or a saccharide group), or where a ring oxygen has been replaced by sulfur, nitrogen, a methylene group, etc. Polysaccharides may be chemically altered, for example, to improve anti-thrombotic function. Such modifications may include, but are not limited to, sulfation, polysulfation, esterification, and methylation.

By "fragment" is meant a molecule containing a part of the intact full-length sequence and structure. In some instances, a fragment of a polysaccharide may be generated by degradation (e.g., hydrolysis, depolymerization) of a larger polysaccharide. Active fragments of a polysaccharides of the invention may include about 2-20 saccharide units of the full-length polysaccharide, such as about 5-10 saccharide units of the full-length molecule, and including any integer between 2 saccharide units and the full-length molecule, so long as the fragment retains biological activity. A fragment of a polypeptide can include a C-terminal deletion, an N-terminal deletion, or an internal deletion of the native polypeptide. Active fragments of a particular protein may include, in some embodiments, about 5-10 contiguous amino acid residues of the full-length molecule or more, such as about 15-25 contiguous amino acid residues of the full-length molecule or more, such as about 20-50 contiguous amino acid residues of the full-length molecule or more, and including any integer between 5 amino acids and the full-length sequence, so long as the fragment in question retains biological activity, such as for example, binding to antithrombin III, anti-thrombotic activity or the ability to inactivate factor IIa and factor Xa activity.

By "substantially purified" is meant the isolation of a substance (e.g., non-anticoagulant sulfated polysaccharide) such that the substance includes the majority of the sample in which it resides. For example, a sample that is substantially purified contains 50% or more of the substance of interest, such as 60% or more of the substance of interest, such as 75% or more of the substance of interest, such as 90% or more of the substance of interest, such as 95% or more of the substance of interest, including 99% or more of the substance of interest. Any convenient protocol may be employed for purifying polysaccharides, polynucleotides, and polypeptides of interest and include, but are not limited to, ultrafiltration, selective precipitation, crystallization, ion-exchange chromatography, affinity chromatography and sedimentation according to density.

By "isolated" is meant, when referring to a polysaccharide or polypeptide, that the indicated molecule is separate and discrete from the whole organism with which the molecule is found in nature or is present in the substantial absence of other biological macro-molecules of the same type.

By "homology" is meant the percent identity between two polypeptide moieties. As referred to herein, two polypeptide sequences are "substantially homologous" to each other when the sequences exhibit about 50% or more sequence identity, such as 60% or more sequence identity, such as 75% or more sequence identity, such as 85% or more sequence identity, such as 90% or more sequence identity, such as 95% or more sequence identity, including 99% or more sequence identity. In some embodiments, substantially homologous polypeptides include sequences having complete identity to a specified sequence.

By "identity" is meant an exact subunit to subunit correspondence of two polymeric sequences. For example, an identical polypeptide is one that has an exact amino acid-to-amino acid correspondence to another polypeptide or an identical polynucleotide is one that has an exact nucleotide-to-nucleotide correspondence to another polynucleotide. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Any convenient protocol may be employed to determine percent identity between two polymeric sequences, such as for example, ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are of interest.

The term "patient," is used in its conventional sense to refer to a living organism suffering from or prone to a condition that can be prevented or treated by administration of a low molecular weight heparin of the invention, and includes both humans and non-human animals.

By "biological sample" is meant a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

By "therapeutically effective dose or amount" is meant an amount that, when administered as described herein, brings about the desired therapeutic response, such as for example, anti-thrombotic activity or increased clotting times.

By "thromboembolic disease" is meant any disorder resulting from the formation of a clot within a blood vessel which interferes with the blood supply to tissues and can cause circulatory system problems, such as for example, deep vein thrombosis, pulmonary embolisms, heart attacks or strokes. As discussed below, thromboembolic diseases may include, but are not limited to, those thromboembolic diseases associated with myocardial infarction, deep vein thrombosis following surgery, transient ischemic attack, coronary artery bypass graft, peripheral vascular disease, stroke percutaneous transluminal coronary angioplasty, acute promyelocytic leukemia, diabetes, multiple myelomas, septic shock, purpura fulminanas, adult respiratory distress syndrome, angina, insertion and the presence of aortic valve or vascular prosthesis, cardiac catherization, transluminal endoplasty, heart valve replacement.

DETAILED DESCRIPTION

Aspects of the invention include methods for treating a thromboembolic disease in a subject. In practicing methods according to certain embodiments, an amount of a low molecular weight heparin (LMWH) and a synergistically effective combination of two or more gastrointestinal epithelial barrier permeation enhancers is orally administered to a subject in a manner sufficient to treat the thromboembolic disease in the subject. Compositions and kits for practicing methods of the invention are also described.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In further describing the subject invention, methods for treating a thromboembolic disease by orally administering a low molecular weight heparin and a synergistically effective combination of two or more gastrointestinal epithelial barrier permeation enhancers are described first in greater detail. Next, compositions and kits for practicing methods of the subject invention are also described.

Methods for Treating a Thromboembolic Disease in a Subject

As summarized above, aspects of the invention include orally administering to a subject an amount of a low molecular weight heparin and a synergistically effective combination of two or more gastrointestinal epithelial barrier permeation enhancers in a manner sufficient to treat a thromboembolic disease in a subject. The term "treating a thromboembolic disease" is used in its conventional sense to refer to reducing or eliminating undesired thrombosis in the subject, such as by reducing the initiation (i.e., increasing the amount time for thrombosis to begin) of blood coagulation as well as the overall rate of blood coagulation of the subject (i.e., increasing the amount of time for blood coagulation to complete). In some embodiments, the methods reduce the initiation of blood coagulation. For example, methods of the invention may increase the amount of time required for the blood to begin coagulating by 5% or more, such as by 10% or more, such as by 25% or more, such as by 50% or more, such as by 75% or more, such as by 90% or more, such as 95% or more, as compared to a suitable control, where in some instances the increase is 200% or less, such as 100% or less. In other embodiments, methods of the invention reduce the rate of blood coagulation. For example, methods of the invention may reduce the rate of blood coagulation by 2% or more, such as by 5% or more, such as by 10% or more, such as by 25% or more, such as by 50% or more, such as by 75% or more, such as by 100% or more, such as by 200% or more, including by 500% or more, where in some instances the increase is 1000% or less, such as 750% or less as compared to a suitable control.

In embodiments of the present invention, an amount of a low molecular weight heparin is orally administered to a subject with a synergistically effective combination of two or more gastrointestinal epithelial barrier permeation enhancers. Depending on the physiology of the subject, the phrase "gastrointestinal epithelial" as used herein, refers to the epithelial tissue of the digestive tract, such as the stomach and intestinal tract (e.g., duodenum, jejunum, ileum), and may further include other structures which participate in the gastrointestinal functions of the body including the lower part of the esophagus, the rectum and the anus. By gastrointestinal permeation enhancer is meant a compound that, when orally administered, increases the amount of low molecular weight heparin that is resorbed by the gastrointestinal system. Furthermore, gastrointestinal permeation enhancers may also accelerate the initiation (i.e., reducing the amount time for resorption to begin) of low molecular weight heparin resorption through the gastrointestinal epithelium as well as accelerate the overall rate of transport of the low molecular weight heparin across the gastrointestinal epithelium of the subject (i.e., reducing the amount of time for low molecular weight heparin resorption by the gastrointestinal system to be complete).

A synergistically effective combination of two or more gastrointestinal epithelial barrier permeation enhancers is employed to increase the amount of low molecular weight heparin resorbed by the gastrointestinal system. For example, the synergistically effective combination of two or more gastrointestinal epithelial barrier permeation enhancers may increase the amount of low molecular weight heparin resorbed by the gastrointestinal system by 5% or more, such as by 10% or more, such as by 25% or more, such as by 50% or more, such as by 75% or more, such as by 90% or more, such as 95% or more, where in some instances the increase is 100% or less, as compared to a suitable control. In other embodiments, the synergistically effective combination of two or more gastrointestinal epithelial barrier permeation enhancers accelerate the initiation of low molecular weight heparin resorption through the gastrointestinal epithelium. For example, gastrointenstinal epithelial barrier permeation enhancers may reduce the amount of time required to initiate resorption of the low molecular weight heparin by 5% or more, such as by 10% or more, such as by 25% or more, such as by 50% or more, such as by 75% or more, such as by 90% or more, such as 95% or more, where in some instances the increase is 100% or less, as compared to a suitable control. In yet other embodiments, the synergistically effective combination or two or more gastrointestinal epithelial barrier permeation enhancers of the invention increases the rate of resorption of the low molecular weight heparin by the gastrointestinal system. For example, gastrointestinal epithelial barrier permeation enhancers may increase the rate of low molecular weight heparin resorption by 2% or more, such as by 5% or more, such as by 10% or more, such as by 25% or more, such as by 50% or more, such as by 75% or more, such as by 100% or more, such as by 200% or more, including by 500% or more, where in some instances the increase is 1000% or less, as compared to a suitable control. In some instances, the synergistically effective combination of two or more gastrointestinal epithelial permeation enhancers of the invention increase the resorption of low molecular weight heparin as determined by Caco-2 cell models, as described in greater detail below. For example, gastrointestinal epithelial barrier permeation enhancers of the invention may increase the resorption of low molecular weight heparin as determined by Caco-2 cell models by 2% or more, such as by 5% or more, such as by 10% or more, such as by 25% or more, such as by 50% or more, such as by 75% or more, such as by 100% or more, such as by 200% or more, including by 500% or more, where in some instances the increase is 1000% or less, as compared to a suitable control.

Gastrointestinal epithelial barrier permeation enhancers may vary, depending on the particular blood coagulation disorder, the physiology of the subject and the desired enhancement of resorption by the gastrointestinal system. In some embodiments, the synergistically effective combination of two or more gastrointestinal epithelial barrier permeation enhancers include one or more tight junction modulators. The term "tight junction" is employed in it conventional sense to refer to the closely associated cellular areas where membranes of adjacent cells are joined together. As such, in certain embodiments, methods of the invention include orally administering a composition having an amount of a low molecular weight heparin with a synergistically effective combination of two or more compounds which modulate the permeation of the low molecular weight heparin through the tight junctions of the gastrointestinal epithelium. By "modulates" is meant modifying or increasing the permeation of the low molecular heparin through the tight junctions of the gastrointestinal epithelium. As such, tight junction modulators modify or increase the resorption of low molecular weight heparins by the gastrointestinal system. In embodiments of the invention, tight junction modulators may include, but are not limited to enzymes, bile acids, polysaccharides, fatty acids and salts thereof and any combination thereof.

In some instances, tight junction modulators are polysaccharides. For example, the polysaccharide tight junction modulator may be chitosan. Chitosan, as used herein refers to the linear copolymer of 2-acetamide-2-deoxy-β-D-glucopyranose and 2-amino-β-D-glucopyranose produced by the N-deactylation of chitin. Polysaccharide tight junction modulators may also include derivatives of chitosan such as N-alkyl chitosan, acylated chitosan, carboxymethyl chitosan, phosphorylated chitosan, N-(aminoalkyl)chitosan, succinyl chitosan and octanoyl chitosan. In certain embodiments, the polysaccharide tight junction modulator is unmodified chitosan. As described above, the term "unmodified chitosan" is used in its conventional sense to refer to chitosan which has not been chemically derivatized or modified in any way to enhance or otherwise change chemical structure. As such, unmodified chitosan is chitosan which has not been modified to include any other foreign moieties, such as for example by sulfation, acetylation, glycosylation, phosphorylation, polymer conjugation (such as with polyethylene glycol). For example, unmodified chitosan exclude chitosans which have been thiolated (such as, for example, chitosan-thio-butylamidine) to provide sulfhydryl groups or methylated (such as, for example, N-trimethyl-chitosan) to provide methyl groups fixed to the surface of the polysaccharide structure. Likewise, unmodified chitosans exclude derivatives of chitosan such as N-alkyl chitosan, acylated chitosan, phosphorylated chitosan, N-(aminoalkyl) chitosan, succinyl chitosan and octanoyl chitosan, as well as chitosan modified with polypeptides, other polysaccharides, cyclodextrins, crown ethers and glass beads or nanoparticles, among others.

In other instances, tight junction modulators are bile acids. The term "bile acid" is used in its conventional sense to refer to the steroidal acids and salts thereof commonly found in the bile of mammals. Suitable bile acids may include, but are not limited to, cholic acid (cholate), deoxycholic acid (deoxycholate), chenodeoxycholic acid (chenodeoxycholate), ursodeoxycholic acid (ursodeoxycholate), glycocholic acid (glycocholate), taurocholic acid (taurocholate) and lithocholic acid (lithocholate), among others. In certain embodiments, the combination of two or more gastrointestinal epithelial barrier permeation enhancers includes deoxycholate.

In other instances, tight junction modulators are enzymes. For example, the enzyme tight junction modulators may be a protease, such as bromelain, trypsin, papain or an enzymatic fragment thereof. In certain embodiments, the combination of two or more gastrointestinal epithelial barrier permeation enhancers includes bromelain. Bromelain, as used herein refers to the group of enzymes commonly derived from the fruit, stem and leaves of *Ananas comosus* and may also include elements such as cysteine proteases, amylase, acid phosphatase, peroxidases and cellulases.

In yet other instances, tight junction modulators are fatty acids and fatty acid salts thereof. Fatty acid tight junction modulators of the invention may vary, and may include any one or a combination of medium chain fatty acids, such as for example C8 (caprylate), C10 (caprate) and C12 (laurate) fatty acids and fatty acid salts thereof. In certain instances, for example, the combination of two or more gastrointenstial epithelial barrier enhancer includes sodium caprate.

In embodiments of the invention, the combination of two or more gastrointestinal epithelial barrier permeation enhancers is a synergistically effective combination of gastrointestinal epithetial barrier permeation enhancers. By "synergistically effective" is meant that the combination of gastrointestinal epithelial barrier permeation enhancers produces an effect (i.e., enhances gastrointestinal epithelial barrier permeation) which is greater than would be achieved by the arithmetic sum of the individual gastrointestinal epithetial barrier permeation enhancers. For example, the synergistically effective combination of two or more gastrointestinal epithelial barrier permeation enhancers produces an effect that is 1.5-fold or greater than would be achieved by the arithmetic sum of the individual gastrointestinal epithelial barrier permeation enhancers, such as 2-fold or greater, such as 3-fold or greater, such as 4-fold or greater, such as 5-fold or greater, such as 10-fold or greater and including 25-fold or greater (and in some instances is 100-fold or less, such as 50-fold or less) than would achieved with the sum the individual gastrointestinal epithelial barrier permeation enhancers. As such, where two gastrointestinal epithelial barrier permeation enhancers are combined, synergistically effective combinations as provided by the present invention produce an effect which is 1.5-fold or greater, such as 2-fold or greater, such as 5-fold or greater, such as 10-fold or greater and including 25-fold or greater than would be achieved by the sum of the two individual gastrointestinal epithelial barrier permeation enhancers. Likewise, where three gastrointestinal epithelial barrier permeation enhancers are combined, synergistically effective combinations of the present invention produce an effect which is 2-fold or greater, such as 5-fold or greater, such as 10-fold or greater and including 25-fold or greater than would be achieved by the sum of the three individual gastrointestinal epithelial barrier permeation enhancers. In some instances, the magnitude of increase is 1000-fold or less, such as 750-fold or less, including 500-fold or less, e.g., 250-fold or less, including 100-fold or less.

For example, where an enzyme tight junction modulator (e.g., bromelain) and a polysaccharide tight junction modulator (e.g., unmodified chitosan) are employed together in methods of the invention, the combination produces an effect (i.e., enhances gastrointestinal epithelial barrier permeation of the low molecular weight heparin) which is greater than would be achieved by the arithmetic sum of the enzyme tight junction modulator (e.g., bromelain) alone plus the polysaccharide tight junction modulator (e.g., unmodified chitosan) alone. In these embodiments, synergistically effective combinations of an enzyme tight junction modulator and a polysaccharide tight junction modulator produce an effect which is 2-fold or greater, such as 5-fold or greater, such as 10-fold or greater and including 25-fold or greater than would be achieved by the arithmetic sum of the enzyme tight junction modulator alone plus the polysaccharide tight junction modulator alone.

Likewise, where a bile acid tight junction modulator (e.g., deoxycholate) and a fatty acid tight junction modulator (e.g., sodium caprate) are employed together in methods of the invention, the combination enhances gastrointestinal epithelial barrier permeation of the low molecular weight heparain which is greater than would be achieved by the arithmetic sum of the bile acid tight junction modulator alone plus the fatty acid tight junction modulator alone. In these embodiments, synergistically effective combinations of a bile acid tight junction modulator and a fatty acid tight junction modulator produce an effect which is 2-fold or greater, such as 5-fold or greater, such as 10-fold or greater and including 25-fold or greater than would be achieved by the arithmetic sum of the bile acid tight junction modulator alone plus the fatty acid tight junction modulator alone.

The concentration of each gastrointestinal epithelial barrier permeation enhancer in the synergistically effective combination may vary depending on the effects as desired as well as the type of gastrointestinal epithelial barrier permeation enhancers combined. The concentration of each gastrointestinal epithelial barrier permeation enhancer in the synergistically effective combination may be 0.01% or more of the total mass of the composition, such as 0.1% or more, such as 1% or more, such as 2% or more, such as 5% or more, such as 10% or more, such as 15% or more, such as 20% or more, such as 25% or more and including 50% or more of the total mass of the composition. In other embodiments, the concentration of each gastrointestinal epithelial barrier permeation enhancer in the combination is 0.01 mg/mL or more, such as 0.05 mg/mL or more, such as 0.1 mg/mL or more, such as 1 mg/mL or more and including 5 mg/mL or more. In yet other embodiments, the concentration of each gastrointestinal epithelial barrier permeation enhancer in the combination is 0.1 mM or more, such as 0.5 mM or more, such as 1 mM or more, such as 5 mM or more, such as 10 mM or more, such as 25 mM or more and including 50 mM or more.

The mass percentage of each gastrointestinal epithelial barrier permeation enhancer in the synergistically effective combination of two or more gastrointestinal epithelial barrier permeation enhancers may vary, ranging from 1% or more of the total mass of the composition, such as 2% or more, such as 5% or more, such as 10% or more, such as 25% or more and including 50% or more of the total mass of the composition. For example, where the synergistically effective combination of gastrointestinal epithelial barrier permeation enhancers includes two gastrointestinal epithelial barrier permeation enhancers, the mass ratio of the first gastrointestinal epithelial barrier permeation enhancer and the second gastrointestinal epithelial barrier permeation enhancer may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the first gastrointestinal epithelial barrier permeation enhancer to the second gastrointestinal epithelial barrier permeation enhancer may range between 1:1 and 1:10; 1:5 and 1:25; 1:10 and 1:50; 1:25 and 1:100; 1:50 and 1:500; or 1:100 and 1:1000. In some embodiments, the mass ratio of the second gastrointestinal epithelial barrier permeation enhancer to the first gastrointestinal epithelial barrier permeation enhancer ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the second gastrointestinal epithelial barrier permeation enhancer to the first gastrointestinal epithelial barrier permeation enhancer may range between 1:1 and 1:10; 1:5 and 1:25; 1:10 and 1:50; 1:25 and 1:100; 1:50 and 1:500; or 1:100 and 1:1000.

In certain embodiments, synergistically effective combinations of the present invention include a combination of chitosan and bromelain. In some instances, chitosan is unmodified chitosan. The concentration of chitosan may vary, ranging from about 0.1% w/v to about 5% w/v, such as about 0.15% w/v to about 4.5% w/v, such as 0.2% w/v to about 4% w/v, such as about 0.25% w/v to about 3.5% w/v, such as 0.3% w/v to about 3% w/v, such as 0.5% w/v to about 2.5% w/v, such as 0.5% w/v to 1.5% w/v, including about 3% w/v. Likewise, the concentration of bromelain may vary, ranging from about 0.01 mg/mL to about 1.0 mg/mL, such as about 0.2 mg/mL to about 0.9 mg/mL, such as 0.25 mg/mL to about 0.75 mg/mL, such as about 0.3 mg/mL to about 0.6 mg/mL, including about 0.4 mg/mL to about 0.5 mg/mL. As such, the weight percent of bromelain in compositions of the invention may range from about 0.01% w/v to about 1% w/v, such as about 0.2% w/v to about 0.9% w/v, such as about 0.25% w/v to about 0.75% w/v, such as about 0.3% w/v to about 0.6% w/v and including about 0.4% w/v to about 0.5% w/v. In certain instances, synergistically effective combinations of bromelain and chitosan include a combination of 0.5 mg/mL bromelain and 3% w/v chitosan, 0.25 mg/mL bromelain and 1.5% w/v chitosan or 0.12 mg/mL bromelain and 0.75% w/v chitosan. As such, the mass ratio of the chitosan and the bromelain may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the chitosan to the bromelain may range between 1:1 and 1:10; 1:5 and 1:25; 1:10 and 1:50; 1:25 and 1:100; 1:50 and 1:500; or 1:100 and 1:1000. In some embodiments, the mass ratio of the bromelain to the chitosan ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the bromelain to the chitosan may range between 1:1 and 1:10; 1:5 and 1:25; 1:10 and 1:50; 1:25 and 1:100; 1:50 and 1:500; or 1:100 and 1:1000. In these embodiments, the synergistically effective combination of chitosan and bromelain has a greater effect on enhancing permeation through the gastrointestinal epithelial barrier than is achieved by the arithmetic sum of chitosan and bromelain individually. For example, in some instances, the combination of chitosan and bromelain enhances permeation through the gastrointestinal epithelial barrier by 2-fold or greater, such as 5-fold or greater, such as 10-folder or greater and including 25-fold or greater than is achieved by the arithmetic sum of chitosan and bromelain individually. As such, in these embodiments, methods include administering a low molecular weight heparin with a synergistically effective combination of chitosan and bromelain. For example, methods may include administering a low molecular weight heparin such as Ardeparin, Bemiparin, Bioparin, Certoparin, Dalteparin, Enoxaparin, Miniparin, Nadroparin, Pamaparin, Reviparin, Sandoparin and Tinzaparin and combinations thereof with a synergistically effective combination of chitosan and bromelain.

In some embodiments, synergistically effective combinations of gastrointestinal epithelial barrier permeation enhancers result from specific amounts of each gastrointestinal epithelial barrier permeation enhancer in combination with the low molecular weight heparin. In other words, a synergistic permeation enhancement effect is provided in these embodiments by a specific amount of each gastrointestinal epithelial barrier permeation enhancer in the combination. For example, where the gastrointestinal epithelial barrier permeation enhancers are bromelain and unmodified chitosan, a synergistic permeation enhancement effect is provided where bromelain is in an amount ranging from 0.1 mg/mL to about 0.5 mg/mL, such as 0.15 mg/mL to about 0.4 mg/mL, including 0.5 mg/mL and unmodified chitosan is in an amount ranging 1% w/v to about 5% w/v, such as about 1.25% w/v to about 4.5% w/v, such as 1.5% w/v to about 4% w/v, such as about 1.75% w/v to about 3.5% w/v, such as 2% w/v to about 3.25% w/v, and including about 3% w/v. In certain instances, a synergistic permeation enhancement effect is provided where bromelain is in an amount of 0.5 mg/mL and unmodified chitosan is in an amount of 3% w/v. In other instances, a synergistic permeation enhancement effect is provided where bromelain is in an amount of 0.25 mg/mL and unmodified chitosan is in an amount of 1.5% w/v. In yet other embodiments, a synergistic permeation enhancement effect is provided where bromelain is in an amount of 0.12 mg/mL and unmodified chitosan is in an amount of 0.75% w/v.

In other embodiments, synergistically effective combinations of gastrointestinal epithelial barrier permeation enhancers result from specific ratios of gastrointenstinal epithelial barrier permeation enhancers with the low molecular weight heparin. In other words, a synergistic permeation enhancement effect is provided in these embodiments by a specific ratio of the gastrointestinal epithelial barrier permeation enhancers in the combination. For example, where the gastrointestinal epithelial barrier permeation enhancers are bromelain and unmodified chitosan, a synergistically effective combination of bromelain and unmodified chitosan may include a ratio of unmodified chitosan to bromelain ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof.

Depending on the gastrointestinal epithelial barrier permeation enhancers, physiology of the subject and type of low molecular weight heparin being administered, each gastrointestinal epithelial barrier permeation enhancer in the combination of two or more gastrointestinal epithelial barrier permeation enhancers may be administered simultaneously or at different times (i.e., sequentially in either order). In other words, the combination of two or more gastrointestinal epithelial barrier permeation enhancers may be administered one gastrointestinal epithelial barrier permeation enhancer followed by another or the two or more gastrointestinal epithelial barrier permeation enhancers may be administered at the same time. For example, two or more tight junction modulators may be employed in combination with a low molecular weight heparin, such as three or more tight junction modulators, including four or more tight junction modulators. Any combination of tight junction modulators may be employed, such as for example, a polysaccharide and a protease, a fatty acid and polysaccharide, a polysaccharide and a bile acid, a polysaccharide, a fatty acid and a bile acid, two different polysaccharides or two different bile acids, among other combinations.

As described above, methods include treating or preventing a thromboembolic disease by orally administering a low molecular weight heparin with a synergistically effective combination of two or more gastrointestinal epithelial barrier permeation enhancers to a subject are provided. By "subject" is meant the person or organism receiving the thromboembolic disease treatment. As such, subjects of the invention may include but are not limited to humans and other primates, such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

In certain embodiments, the subject is a human. For example, the subject methods may be employed to treat or prevent a thromboembolic disease in a human, such as where the thromboembolic disease is associated with myocardial infarction, deep vein thrombosis following surgery, transient ischemic attack, coronary artery bypass graft, peripheral vascular disease, stroke percutaneous transluminal coronary angioplasty, acute promyelocytic leukemia, diabetes, multiple myelomas, septic shock, purpura fulminanas, adult respiratory distress syndrome, angina, insertion and the presence of aortic valve or vascular prosthesis, cardiac catherization, transluminal endoplasty, heart valve replacement.

Aspects of the invention include orally administering to a subject a composition having an amount of a low molecular weight heparin with a synergistically effective combination of two or more gastrointestinal epithelial barrier permeation enhancers to treat or prevent a thromboembolic disease. As described above, the term "low molecular weight heparin" is used in its conventional sense to refer to the class of short chain sulfated glycosaminoglycan anticoagulant compounds having an average molecular weight ranging from 2 kDa to 12 kDa which are obtained by fractionation or depolymerization of unfractionated naturally occurring polymeric heparin. In some embodiments, low molecular weight heparins may be derived from heparin obtained from a biological source. By "biological source" is meant a naturally-occurring organism or part of an organism. For example, low molecular weight heparin of interest may be fractionated or depolymerized from unfractionated heparin extracted from mucosal tissues of slaughtered meat animals such as porcine intestine or bovine lung. Any convenient protocol can be employed for extracting the low molecular weight heparin from the biological source. For instance, the low molecular weight heparin can be extracted from the biological source by acid-base extraction, enzymatic degradation, selective precipitation, filtration, among other procedures. In some instances, the low molecular weight heparin may be a low molecular weight fragment of unfractionated polymeric heparin formed by enzymatic or chemical depolymerization.

In other embodiments, low molecular weight heparins are synthetic low molecular weight heparins. By "synthetic" is meant that the low molecular weight heparin is partially or wholly produced by man-made methods (e.g., chemical synthesis). For example, the synthetic low molecular weight heparin may be a sulfated oligomer, such as a sulfated oligosaccharide.

For example, low molecular weight heparins may include but are not limited to Ardeparin, Bemiparin, Bioparin, Certoparin, Dalteparin, Enoxaparin, Miniparin, Nadroparin, Parnaparin, Reviparin, Sandoparin and Tinzaparin and combinations thereof.

Depending on the desired effects and potency of the low molecular weight heparin, one or more low molecular weight heparins may employed together. For example, two or more low molecular weight heparins may be employed together, such as three or more low molecular weight heparins and including four or more low molecular weight heparins. Where more than one low molecular weight heparins is employed, all of the low molecular weight heparins may be natural low molecular weight heparins, all synthetic low molecular weight heparins or any combination thereof. Where more than one low molecular weight heparin is employed, the mass percentage of each low molecular weight heparin in the composition may vary, ranging from 1% or more of the total mass of the composition, such as 2% or more, such as 5% or more, such as 10% or more, such as 25% or more and including as 50% or more of the total mass of the composition.

The mass ratio of the low molecular weight heparin and the synergistically effective combination of two or more gastrointestinal epithelial barrier permeation enhancers may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the low molecular weight heparin to the synergistically effective combination of two or more gastrointestinal epithelial barrier permeation enhancers may range between 1:1 and 1:10; 1:5 and 1:25; 1:10 and 1:50; 1:25 and 1:100; 1:50 and 1:500; or 1:100 and 1:1000. In some embodiments, the mass ratio of the synergistically effective combination of two or more gastrointestinal epithelial barrier permeation enhancers to the low molecular weight heparin ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the synergistically effective combination of two or more gastrointestinal epithelial barrier permeation enhancers to the low molecular weight heparin may range between 1:1 and 1:10; 1:5 and 1:25; 1:10 and 1:50; 1:25 and 1:100; 1:50 and 1:500; or 1:100 and 1:1000.

The low molecular weight heparin and synergistically effective combination of two or more gastrointestinal epithelial barrier permeation enhancers may be administered to the subject in any order. In some instances, the low molecular weight heparin is orally administered prior to orally administering the combination of two or more gastrointestinal epithelial barrier permeation enhancers. In other instances, the low molecular weight heparin is orally administered after orally administering the combination of two or more gastrointestinal epithelial barrier permeation enhancers. In yet other instances, the low molecular weight heparin is orally administered in conjunction (i.e., simultaneously) with orally administering the combination of two or more gastrointestinal epithelial barrier permeation enhancers. If both the low molecular weight heparin and the combination of two or more gastrointestinal epithelial barrier permeation enhancers are provided at the same time, each can be provided in the same or in a different composition. Where the low molecular weight heparin and the combination of two or more gastrointestinal epithelial barrier permeation enhancers are administered at the same time, the low molecular weight heparin may be mixed with the combination of two or more gastrointestinal epithelial barrier permeation enhancers before administering the composition to the subject. Any convenient mixing protocol may be used, such as by dry shaking, solution or suspension mixing, industrial mixing protocols and the like. Thus, low molecular weight heparin and combination of two or more gastrointestinal epithelial barrier permeation enhancers can be presented to the individual by way of concurrent therapy. By "concurrent therapy" is intended administration to a subject such that the therapeutic effect of the combination of the low molecular weight heparin and gastrointestinal epithelial barrier permeation enhancer is caused in the subject undergoing therapy. Similarly, one or more low molecular weight heparins and two or more gastrointestinal epithelial barrier permeation enhancers can be orally administered in at least one therapeutic dose.

Any suitable combination of low molecular weight heparin and two or more gastrointenstinal epithelial barrier permeation enhancers may be administered, so long as the combination of gastrointestinal epithelial barrier permeation enhancer provides a synergistic permeation enhancement effect, as described above. In certain embodiments, methods include administering a low molecular weight heparin with a synergistically effective combination of two or more of sodium caprate, deoxycholate, bromelain and chitosan. For example, methods may include administering a low molecular weight heparin with a synergistically effective combination of bromelain and chitosan. For instance, one or more of Ardeparin, Bemiparin, Bioparin, Certoparin, Dalteparin, Enoxaparin, Miniparin, Nadroparin, Parnaparin, Reviparin, Sandoparin and Tinzaparin may be administered with a synergistically effective combination of bromelain and chitosan.

Low molecular weight heparins with a synergistically effective combination of two or more gastrointestinal epithelial barrier permeation enhancers as disclosed herein can be administered alone (i.e., as single agents), or in combination with other therapeutic agents, such as other anticoagulating or anti-thrombotic agents. As desired, an amount of a low molecular weight heparin with a combination gastrointestinal epithelial barrier permeation enhancers may be employed in the treatment of a subject that has been diagnosed as having a thromboembolic disease, such as for example a subject diagnosed as having a thromboembolic disease associated with myocardial infarction, deep vein thrombosis following surgery, transient ischemic attack, coronary artery bypass graft, peripheral vascular disease, stroke percutaneous transluminal coronary angioplasty, acute promyelocytic leukemia, diabetes, multiple myelomas, septic shock, purpura fulminanas, adult respiratory distress syndrome, angina, insertion and the presence of aortic valve or vascular prosthesis, cardiac catherization, transluminal endoplasty, heart valve replacement.

In practicing methods of the invention, protocols for treating or preventing a thromboembolic disease in a subject may vary, such as for example by age, weight, severity of the blood clotting disorder, the general health of the subject, as well as the particular composition and concentration of the low molecular weight heparin and gastrointestinal epithelial barrier permeation enhancers being administered. The concentration of low molecular weight heparins achieved in a subject following oral administration and resorption by the gastrointestinal system may vary, in some instances, ranging from 0.01 nM to 500 nM. Low molecular weight heparins of interest are anti-thrombotic and anticoagulant at their optimal concentration. By "optimal concentration" is meant the concentration in which low molecular weight heparins exhibit the highest amount of anticoagulant activity. As such, depending on the potency of the low molecular weight heparin as well as the desired effect, the optimal concentration of low molecular weight heparins provided by methods of the invention may range, from 0.01 nM to 500 nM, such as 0.1 nM to 250 nM, such as 0.1 nM to 100 nM, such as 0.1 nM to 75 nM, such as 0.1 nM to 50 nM, such as 0.1 nM to 25 nM, such as 0.1 nM to 10 nM, and including 0.1 nM to 1 nM. Likewise, the concentration of gastrointestinal epithelial barrier permeation enhancers achieved in a subject following oral administration and resorption by the gastrointestinal system may vary, in some instances, ranging from 0.01 nM to 500 nM. For example, depending on the inherent absorptivity of the low molecular weight heparin as well as the desired effect, the concentration of gastrointestinal epithelial barrier permeation enhancers provided by methods of the invention may range, from 0.01 nM to 500 nM, such as 0.1 nM to 250 nM, such as 0.1 nM to 100 nM, such as 0.1 nM to 75 nM, such as 0.1 nM to 50 nM, such as 0.1 nM to 25 nM, such as 0.1 nM to 10 nM, and including 0.1 nM to 1 nM.

Therefore, the oral dosage of compositions containing a low molecular weight heparin with a combination of two or more gastrointestinal epithelial barrier permeation enhancers of interest may vary, ranging from about 0.01 mg/kg to 500 mg/kg per day, such as from 0.01 mg/kg to 400 mg/kg per day, such as 0.01 mg/kg to 200 mg/kg per day, such as 0.1 mg/kg to 100 mg/kg per day, such as 0.01 mg/kg to 10 mg/kg per day, such as 0.01 mg/kg to 2 mg/kg per day, including 0.02 mg/kg to 2 mg/kg per day. In other embodiments, the oral dosage may range from 0.01 to 100 mg/kg four times per day (QID), such as 0.01 to 50 mg/kg QID, such as 0.01 mg/kg to 10 mg/kg QID, such as 0.01 mg/kg to 2 mg/kg QID, such as 0.01 to 0.2 mg/kg QID. In other embodiments, the oral dosage may range from 0.01 mg/kg to 50 mg/kg three times per day (TID), such as 0.01 mg/kg to 10 mg/kg TID, such as 0.01 mg/kg to 2 mg/kg TID, and including as 0.01 mg/kg to 0.2 mg/kg TID. In yet other embodiments, the oral dosage may range from 0.01 mg/kg to 100 mg/kg two times per day (BID), such as 0.01 mg/kg to 10 mg/kg BID, such as 0.01 mg/kg to 2 mg/kg BID, including 0.01 mg/kg to 0.2 mg/kg BID. The amount of compound administered will depend on the potency and concentration of the specific low molecular weight heparin, the magnitude or antithrombotic effect desired, the inherent absorptivity of the low molecular weight heparin, as well as the desired enhancement of gastrointestinal resorption.

As discussed above, compositions containing an amount of a low molecular weight heparin and a synergistically effective combination of two or more gastrointestinal epithelial barrier permeation enhancers may be orally administered in combination with other low molecular weight heparins, gastrointestinal epithelial barrier permeation enhancers or other therapeutic agents, such as other antithrombotic agents, blood factors, or other medications according to a dosing schedule relying on the judgment of the clinician and needs of the subject. As such, dosing schedules may include, but are not limited to administration five times per day, four times per day, three times per day, twice per day, once per day, three times per week, twice per week, once per week, twice per month, once per month, and any combination thereof.

In some embodiments, the thromboembolic disease may be a chronic condition requiring the subject methods and compositions in multiple doses over an extended period. Alternatively, methods and compositions of the invention may be administered to treat an acute condition (e.g., thrombosis caused by surgery, heart attack, stroke, pulmonary embolism, etc.) in single or multiple doses for a relatively short period, for example one to two weeks. In practicing embodiments of the invention, one or more therapeutically effective cycles of treatment will be administered to a subject. By "therapeutically effective cycle of treatment" is meant a cycle of treatment that when administered, brings about the desired therapeutic response with respect to treatment. For example, one or more therapeutically effective cycles of treatment may reduce the initiation or rate of thrombosis as determined by blood clotting assays (e.g., CAT, aPTT, described in detail below) by 1% or more, such as 5% or more, such as 10% or more, such as 15% or more, such as 20% or more, such as 30% or more, such as 40% or more, such as 50% or more, such as 75% or more, such as 90% or more, such as 95% or more, including reducing the initiation or rate of thrombosis by 99% or more. In other instances, one or more therapeutically effective cycles of treatment may reduce the initiation or rate of thrombosis by 1.5-fold or more, such as 2-fold or more, such as 5-fold or more, such as 10-fold or more, such as 50-fold or more, including reducing the initiation or rate of thrombosis by 100-fold or more.

In some embodiments, subjects treated by methods of the invention exhibit a positive therapeutic response. By "positive therapeutic response" is meant that the subject exhibits an improvement in one or more symptoms of a thromboembolic disease. For example, a subject exhibiting a positive therapeutic response to methods provided by the invention may include but is not limited to responses such as reduced clot formation times, increased clotting time or a combination thereof. In certain embodiments, more than one therapeutically effective cycle of treatment is administered.

Any convenient mode of administration may be employed so long as the composition is resorbed through the gastrointestinal epithelium. As such, modes of administration may include oral administration (i.e., through the mouth) or by nasogastric tube (e.g., feeding tube or NG-tube). As discussed in greater detail below, pharmaceutical compositions of the invention may be in the form of a liquid solution or suspension, syrup, tablet, capsule, powder, gel, or any combination thereof. Where a composition having an amount of a low molecular weight heparin and a synergistically effective combination of two or more gastrointestinal epithelial barrier permeation enhancers is orally administered to a subject, as discussed in detail above, the mode of administration for the low molecular weight heparin may be the same or different than for the combination of two or more gastrointestinal epithelial barrier permeation enhancers component. For example, in some instances, the low molecular weight heparin is administered orally whereas the combination of two or more gastrointestinal epithelial barrier permeation enhancers is administered by nasogastric tube. In other instances, both the low molecular weight heparin and the combination of two or more gastrointestinal epithelial barrier permeation enhancers are administered orally.

In certain embodiments, methods of the invention provide for orally administering a composition having an amount of a low molecular weight heparin and a synergistically effective combination of gastrointestinal epithelial barrier permeation enhancers prophylactically, such as for example before planned surgery or whenever it is desired to reduce the potential risk for unintentional thrombosis. The composition may be administered prophylactically as desired, such as one hour or more prior to a planned procedure, such as 10 hours prior to a planned procedure, such as 24 hours prior to a planned procedure, and including one week prior to a planned procedure. In some instances, the composition administered prior to or during a planned procedure may be a sustained-release formulation (e.g., sustained release caplets or tablets).

In certain embodiments, compositions of the invention can be orally administered prior to, concurrent with, or subsequent to other agents for treating related or unrelated conditions. If provided at the same time as other agents, compositions of the invention can be provided in the same or in a different composition. Thus, low molecular weight heparins and synergistically effective combinations of two or more gastrointestinal epithelial barrier permeation enhancers of interest and other agents can be presented in an oral dosage form to the individual by way of concurrent therapy. For example, concurrent therapy may be achieved by administering compositions of the invention and a pharmaceutical composition having at least one other agent, such as a antithrombotic agent, anti-inflammatory drug, growth factor modulating agents, hemodynamic modulators or chemotherapeutic agent, which in combination comprise a therapeutically effective dose, according to a particular oral dosing regimen. Similarly, one or more low molecular weight heparins with a synergistically effective combination of two or more gastrointestinal epithelial barrier permeation enhancers and therapeutic agents can be administered in at least one therapeutic dose. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Compositions

Aspects of the invention also include oral dosage compositions for treating or preventing a thromboembolic disease in a subject. In embodiments of the invention, compositions include an amount of a low molecular weight heparin with a synergistically effective combination of two or more gastrointestinal epithelial barrier permeation enhancers. As described in detail above, the synergistically effective combination of two or more gastrointestinal epithelial barrier permeation enhancers is a combination that when orally administered, increase the amount of low molecular weight heparin that is resorbed by the gastrointestinal system in a manner that is greater than would be achieved by the arithmetic sum of the individual gastrointestinal epithetial barrier permeation enhancers. Furthermore, the combination of two or more gastrointestinal permeation enhancers accelerates the initiation (i.e., reducing the amount time for resorption to begin) of low molecular weight heparin resorption through the gastrointestinal epithelium as well as accelerate the overall rate of transport of the low molecular weight heparin across the gastrointestinal epithelium of the subject (i.e., reducing the amount of time for low molecular weight heparin resorption by the gastrointestinal system to be complete).

As noted above, the synergistically effective combination of two or more gastrointestinal epithelial barrier permeation enhancers may increase the amount of low molecular weight heparins resorbed by the gastrointestinal system. For example, the subject combinations of gastrointestinal epithelial barrier permeation enhancers may increase the amount of low molecular weight heparins resorbed by the gastrointestinal system by 5% or more, such as by 10% or more, such as by 25% or more, such as by 50% or more, such as by 75% or more, such as by 90% or more, such as 95% or more, as compared to a suitable control. In other embodiments, the synergistically effective combination of two or more gastrointestinal epithelial barrier permeation enhancers in oral compositions of the invention accelerate the initiation of low molecular weight heparin resorption through the gastrointestinal epithelium. For example, the subject combinations may reduce the amount of time required to initiate resorption of the low molecular weight heparin by 5% or more, such as by 10% or more, such as by 25% or more, such as by 50% or more, such as by 75% or more, such as by 90% or more, such as 95% or more, as compared to a suitable control. In yet other embodiments, the synergistically effective combination of two or more gastrointestinal epithelial barrier permeation enhancers in oral compositions of the invention increase the rate of resorption of the low molecular weight heparin. For example, the subject combinations may increase the rate of low molecular weight heparin resorption by 2% or more, such as by 5% or more, such as by 10% or more, such as by 25% or more, such as by 50% or more, such as by 75% or more, such as by 100% or more, such as by 200% or more, including by 500% or more, as compared to a suitable control.

In certain instances, the synergistically effective combination of two or more gastrointestinal epithelial permeation enhancers in oral compositions of interest may increase the resorption of low molecular weight heparins as determined by Caco-2 cell models. For example, the subject combinations of gastrointestinal epithelial barrier permeation enhancers may increase the resorption as determined by Caco-2 cell models by 2% or more, such as by 5% or more, such as by 10% or more, such as by 25% or more, such as by 50% or more, such as by 75% or more, such as by 100% or more, such as by 200% or more, including by 500% or more, as compared to a suitable control.

As discussed in detail above, oral dosage compositions of the invention include one or more low molecular weight heparins with a synergistically effective combination of two or more gastrointestinal epithelial barrier permeation enhancers. The synergistically effective combination of two or more gastrointestinal epithelial barrier permeation enhancers in the compositions of interest may vary depending on the particular blood coagulation disorder, the physiology of the subject and the desired enhancement of resorption by the gastrointestinal system. In some embodiments, gastrointestinal epithelial barrier permeation enhancers are tight junction modulators. For example, tight junction modulators in oral dosage compositions of the invention may include, but are not limited to enzymes, bile acids, polysaccharides, fatty acids and salts thereof and any combination thereof.

In some instances, tight junction modulators are polysaccharides. For example, the polysaccharide tight junction modulator, in certain instances may be chitosan. Chitosan, as discussed above, refers to the linear copolymer of 2-acetamide-2-deoxy-β-D-glucopyranose and 2-amino-β-D-glucopyranose made by N-deactylation of chitin. Polysaccharide tight junction modulators may also include, derivatives of chitosan such as N-alkyl chitosan, acylated chitosan, carboxymethyl chitosan, thiolated chitosan, phosphorylated chitosan, chitosan cyclodextrin, N-(aminoalkyl)chitosan, succinyl chitosan and octanoyl chitosan, among others. In certain embodiments, the polysaccharide tight junction modulator is unmodified chitosan. As described above, the term "unmodified chitosan" is used in its conventional sense to refer to chitosan which has not been chemically derivatized or modified in any way to enhance or otherwise change chemical structure or properties. As such, unmodified chitosan is chitosan which has not been modified with any other foreign moieties, such as for example by sulfation, acetylation, glycosylation, phosphorylation, polymer conjugation (such as with polyethylene glycol). For example, unmodified chitosan exclude chitosans which have been thiolated (such as, for example, chitosan-thio-butylamidine) to provide sulfhydryl groups or methylated (such as, for example, N-trimethylchitosan) to provide methyl groups fixed to the surface of the polysaccharide structure. Likewise, unmodified chitosans exclude derivatives of chitosan such as N-alkyl chitosan, acylated chitosan, phosphorylated chitosan, N-(aminoalkyl)chitosan, succinyl chitosan and octanoyl chitosan, as well as chitosan modified with polypeptides, other polysaccharides, cyclodextrins, crown ethers and glass beads or nanoparticles, among others.

In other instances, tight junction modulators are bile acids. Suitable bile acid tight junction modulators may include but are not limited to cholic acid (cholate), deoxycholic acid (deoxycholate), chenodeoxycholic acid (chenodeoxycholate), ursodeoxycholic acid (ursodeoxycholate), glycocholic acid (glycocholate), taurocholic acid (taurocholate) and lithocholic acid (lithocholate), among others.

In other instances, tight junction modulators are enzymes. For example, in certain compositions of the invention, the enzyme tight junction modulators is a protease, such as bromelain.

In yet other instances, tight junction modulators are fatty acids and fatty acid salts thereof. Fatty acid tight junction modulators in compositions of the invention may vary, and may include any one or a combination of medium chain fatty acids, such as for example C8 (caprylate), C10 (caprate) and C12 (laurate) fatty acids and fatty acid salts thereof. In certain instances, for example, the fatty acid tight junction modulator is sodium caprate.

In embodiments of the present invention, oral dosage compositions include two or more synergistically effective gastrointestinal epithelial barrier permeation enhancers. For example, compositions may include two or more tight junction modulators, such as three or more tight junction modulators, including four or more tight junction modulators. Compositions may include any combination of tight junction modulators, such as for example, a polysaccharide and a protease, a fatty acid and polysaccharide, a polysaccharide and a bile acid, a polysaccharide, a fatty acid and a bile acid, two different polysaccharides or two different bile acids, among other combinations, so long as the combination of gastrointestinal epithelial barrier permeation enhancer provides a synergistic permeation enhancement effect, as described above.

The concentration of each gastrointestinal epithelial barrier permeation enhancer in the combination may vary. Depending on the gastrointestinal epithelial barrier permeation enhancer, the concentration of each gastrointestinal epithelial barrier permeation enhancer in the combination is 0.01 mg/mL or more, such as 0.05 mg/mL or more, such as 0.1 mg/mL or more, such as 1 mg/mL or more and including 5 mg/mL or more. In yet other embodiments, the concentration of each gastrointestinal epithelial barrier permeation enhancer in the combination is 0.1 mM or more, such as 0.5 mM or more, such as 1 mM or more, such as 5 mM or more, such as 10 mM or more, such as 25 mM or more and including 50 mM or more.

The mass percentage of each gastrointestinal epithelial barrier permeation enhancer in the combination of two or more gastrointestinal epithelial barrier permeation enhancers may vary, ranging from 1% or more of the total mass of the composition, such as 2% or more, such as 5% or more, such as 10% or more, such as 25% or more and including 50% or more of the total mass of the composition. For example, where the combination of gastrointestinal epithelial barrier permeation enhancers includes two gastrointestinal epithelial barrier permeation enhancers, the mass ratio of the first gastrointestinal epithelial barrier permeation enhancer and the second gastrointestinal epithelial barrier permeation enhancer may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the first gastrointestinal epithelial barrier permeation enhancer to the second gastrointestinal epithelial barrier permeation enhancer may range between 1:1 and 1:10; 1:5 and 1:25; 1:10 and 1:50; 1:25 and 1:100; 1:50 and 1:500; or 1:100 and 1:1000. In some embodiments, the mass ratio of the second gastrointestinal epithelial barrier permeation enhancer to the first gastrointestinal epithelial barrier permeation enhancer ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the second gastrointestinal epithelial barrier permeation enhancer to the first gastrointestinal epithelial barrier permeation enhancer may range between 1:1 and 1:10; 1:5 and 1:25; 1:10 and 1:50; 1:25 and 1:100; 1:50 and 1:500; or 1:100 and 1:1000.

In certain instances, the combination of two or more gastrointestinal epithetial barrier permeation enhancers includes a chitosan and a bromelain. In certain instances, the chitosan is unmodified chitosan. Where a chitosan and a bromelain are employed, the mass ratio of the chitosan and the bromelain may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the chitosan to the bromelain may range between 1:1 and 1:10; 1:5 and 1:25; 1:10 and 1:50; 1:25 and 1:100; 1:50 and 1:500; or 1:100 and 1:1000. In some embodiments, the mass ratio of the bromelain to the chitosan ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the bromelain to the chitosan may range between 1:1 and 1:10; 1:5 and 1:25; 1:10 and 1:50; 1:25 and 1:100; 1:50 and 1:500; or 1:100 and 1:1000.

Where compositions of the invention include a combination of chitosan and bromelain, the concentration of chitosan may vary, ranging from about 0.1% w/v to about 5% w/v, such as about 0.15% w/v to about 4.5% w/v, such as 0.2% w/v to about 4% w/v, such as about 0.25% w/v to about 3.5% w/v, such as 0.3% w/v to about 3% w/v, such as 0.5% w/v to about 2.5% w/v, including about 0.5% w/v to 1.5% w/v. Likewise, the concentration of bromelain may also vary, ranging from about 0.01 mg/mL to about 1.0 mg/mL, such as about 0.2 mg/mL to about 0.9 mg/mL, such as 0.25 mg/mL to about 0.75 mg/mL, such as about 0.3 mg/mL to about 0.6 mg/mL, including about 0.4 mg/mL to about 0.5 mg/mL. As such, the weight percent of bromelain in compositions of the invention may range from about 0.01% w/v to about 1% w/v, such as about 0.2% w/v to about 0.9% w/v, such as about 0.25% w/v to about 0.75% w/v, such as about 0.3% w/v to about 0.6% w/v and including about 0.4% w/v to about 0.5% w/v. In certain instances, the concentration of chitosan is about 3% and the concentration of bromelain is about 0.5 mg/mL.

In some embodiments, compositions of interest include synergistically effective combinations of gastrointestinal epithetial barrier permeation enhancers which provide a synergistic permeation enhancement effect as a result of specific amounts of each gastrointenstinal epithelial barrier permeation enhancer in the combination. For example, where the gastrointenstinal epithelial barrier permeation enhancers are bromelain and unmodified chitosan, a synergistically effective combination of bromelain and unmodified chitosan may include bromelain in an amount ranging from 0.1 mg/mL to about 0.5 mg/mL, such as 0.15 mg/mL to about 0.4 mg/mL, including 0.5 mg/mL and unmodified chitosan in an amount ranging 1% to about 5%, such as about 1.25% to about 4.5%, such as 1.5% to about 4%, such as about 1.75% to about 3.5%, such as 2% to about 3.25%, and including about 3%. In certain instances, synergistically effective combinations of bromelain and unmodified chitosan include a combination of 0.5 mg/mL bromelain and 3% w/v unmodified chitosan. In other instances, synergistically effective combinations of bromelain and unmodified chitosan include 0.25 mg/mL bromelain and 1.5% w/v unmodified chitosan. In yet other embodiments, synergistically effective combinations of bromelain and chitosan include 0.12 mg/mL bromelain and 0.75% w/v unmodified chitosan.

In other embodiments, compositions of interest include synergistically effective combinations of gastrointestinal epithetial barrier permeation enhancers which provide a synergistic permeation enhancement effect as a result of specific ratios of gastrointenstinal epithelial barrier permeation enhancers in the combination. For example, where the gastrointenstinal epithelial barrier permeation enhancers are bromelain and unmodified chitosan, a synergistically effective combination of bromelain and unmodified chitosan may include a ratio of unmodified chitosan to bromelain ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof.

As described above, low molecular weight heparins in oral dosage compositions of the invention refer to the class of short chain sulfated glycosaminoglycan anti-thrombotic compounds having an average molecular weight ranging from 2 kDa to 12 kDa which are obtained by fractionation or depolymerization of unfractionated naturally occurring polymeric heparin. The anti-thrombotic properties of low molecular weight heparins may be determined using clotting assays, including calibrated automated thrombography (CAT), dilute prothrombin time (dPT) or activated partial thromboplastin time (aPTT) clotting assays. One measure of anti-thrombotic activity is to compare the low molecular weight heparin in question with the known anticoagulant heparin.

Low molecular weight heparins may be derived from heparin obtained from a biological source. For example, low molecular weight heparins of interest may be fractionated or depolymerized from unfractionated heparin extracted from mucosal tissues of slaughtered meat animals such as porcine intestine or bovine lung. Any convenient protocol can be employed for extracting the low molecular weight heparin from the biological source. For instance, the low molecular weight heparin can be extracted from the biological source by acid-base extraction, enzymatic degradation, selective precipitation, filtration, among other procedures. In some instances, the low molecular weight heparin may be a low molecular weight fragment of unfractionated high molecular weight polymeric heparin formed by enzymatic or chemical depolymerization.

In other embodiments, compositions include synthetic low molecular weight heparins. By "synthetic" is meant that the low molecular weight heparin is partially or wholly produced by man-made methods (e.g., chemical synthesis). For example, the synthetic low molecular weight heparin may be a sulfated oligomer, such as a sulfated oligosaccharide.

For example, low molecular weight heparins may include but are not limited to Ardeparin, Bemiparin, Bioparin, Certoparin, Dalteparin, Enoxaparin, Miniparin, Nadroparin, Parnaparin, Reviparin, Sandoparin and Tinzaparin.

Low molecular weight heparins of interest may range in average molecular weight from about 10 daltons to about 500,000 daltons, such as from about 2000 daltons to 12,000 daltons, such as for example, from 2500 daltons to 10,000 daltons, such as from 3000 daltons to 9500 daltons, such as from 3500 daltons to 9000 daltons, including 4000 daltons to 8500 daltons. Molecular weights of low molecular weight heparins can be determined by any convenient protocol, such as for example, gel permeation chromatography or high-performance size-exclusion chromatography (HPSEC), capillary electrophoresis, PAGE (polyacrylamide gel electrophoresis), agarose gel electrophoresis, among others.

In some embodiments, low molecular weight heparins of interest may be heterogeneous mixtures of short chain heparin molecules having varying molecular weights. For example, in some instances, 5% or more of the low molecular weight heparin composition has a molecular weight that ranges from 10 to 4000 daltons, such as 10% or more, such as 25% or more, such as 50% or more, such as 75% or more, such as 90% or more, including 95% or more of the low molecular weight heparin composition has a molecular weight that ranges from 10 to 4000 daltons. In other embodiments, 5% or more of the low molecular weight heparin composition has a molecular weight that ranges from 4000 daltons to 8000 daltons, such as 10% or more, such as 25% or more, such as 50% or more, such as 75% or more, such as 90% or more, including 95% or more of the low molecular weight heparin composition has a molecular weight that ranges from 4000 to 8000 daltons. In yet other embodiments, 5% or more of the low molecular weight heparin composition has a molecular weight that are greater than 8000 daltons, such as 10% or more, such as 25% or more, such as 50% or more, such as 75% or more, such as 90% or more, including 95% or more of the low molecular weight heparin composition has a molecular weight that is greater than 8000 daltons.

In some embodiments, low molecular weight heparin compositions include low molecular weight heparins extracted from a biological source and have been fractionated to isolate the desired short chain heparin molecules (e.g., fractions containing low molecular weight heparins having molecular weight ranging from 4000-8000 daltons). Any convenient protocol may be used to fractionate low molecular weight heparins of interest, including but not limited to size exclusion chromatography, gel permeation chromatography, capillary electrophoresis, among others.

In certain instances, low molecular weight heparin obtained by fractionating an unfractionated polymeric heparin sample may be employed for treating a thromboembolic disease as provided by the methods and compositions of the invention. For example, low molecular weight heparin are extracted from a biological source to isolate short chain heparin molecules having molecular weights that range from 2000 to 12,000 daltons, such as 2000 to 10,000 daltons, such as 3000 to 9000 daltons, such as 3500 to 8500 daltons, and including 4000 to 8000 daltons. In certain embodiments, one or more of these fractions may be orally administered in combination with the synergistically effective combination of two or more gastrointestinal epithelial barrier permeation enhancers for treating a thromboembolic disease in a subject, such as by the methods described above.

In certain embodiments, low molecular weight heparin may be prepared by enzymatic, acid-hydrolysis or radical depolymerization of unfractionated polymeric heparin. The molecular weight ranges of the resulting products may be adjusted based upon the stringency of the hydrolysis or depolymerization conditions employed. Fractions may then be further purified using ion exchange chromatography.

Hydrolysis reaction times will typically range from 15 minutes to several hours. The resulting hydrolyzed reaction mixture is then neutralized by addition of base (e.g., sodium hydroxide). Salts are subsequently removed, for example, by electrodialysis, and the hydrolysis products are analyzed to determine weight average molecular weight, saccharide content, and sulfur content, using conventional analytical techniques for carbohydrate analysis. Alternatively, enzymatic methods may be employed to degrade unfractionated polymeric heparin using, e.g., glycosidases. Low molecular weight heparins for use in the invention may be heterogeneous or homogeneous, depending upon the degree of separation employed.

Oral dosage compositions of the invention may include one or more low molecular weight heparins, as desired. For example, two or more low molecular weight heparins may be combined, such as three or more low molecular weight heparins and including four or more low molecular weight heparins. Where more than one low molecular weight heparin is combined together, all of the low molecular weight heparins may be natural low molecular weight heparins, all synthetic low molecular weight heparins or any combination thereof. Where oral compositions include more than one low molecular weight heparin, the mass percentage of each low molecular weight heparin in the composition may vary, ranging from 1% or more of the total mass of the composition, such as 2% or more, such as 5% or more, such as 10% or more, such as 25% or more and including as 50% or more of the total mass of the composition.

The amount (i.e., mass) of each of the low molecular weight heparin and the synergistically effective combination of two or more gastrointestinal epithelial barrier permeation enhancers in oral dosage compositions of interest may vary, ranging from 0.001 mg to 1000 mg, such as 0.01 mg to 500 mg, such as 0.1 mg to 250 mg, such as 0.5 mg to 100 mg, such as 1 mg to 50 mg, including 1 mg to 10 mg. As such, the mass ratio of the one or more low molecular weight heparins and the synergistically effective combination or two or more gastrointestinal epithelial barrier permeation enhancers in subject oral dosage compositions may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the low molecular weight heparin to the synergistically effective combination of two or more gastrointestinal epithelial barrier permeation enhancers may range between 1:1 and 1:10; 1:5 and 1:25; 1:10 and 1:50; 1:25 and 1:100; 1:50 and 1:500; or 1:100 and 1:1000. In some embodiments, the mass ratio of the synergistically effective combination of two or more gastrointestinal epithelial barrier permeation enhancers to the low molecular weight heparin ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the synergistically effective combination of two or more gastrointestinal epithelial barrier permeation enhancers to the low molecular weight heparin may range between 1:1 and 1:10; 1:5 and 1:25; 1:10 and 1:50; 1:25 and 1:100; 1:50 and 1:500; or 1:100 and 1:1000.

Oral dosage compositions may be homogeneous, containing only a single type of low molecular weight heparin and a single synergistically effective combination of two or more gastrointestinal epithelial permeation barrier enhancers. In other embodiments, compositions of interest are heterogenous mixtures of two or more low molecular weight heparins or two or more synergistically effective combinations of gastrointestinal epithelial permeation barrier enhancers. For example, heterogenous mixtures may contain two or more different low molecular weight heparins and two or more different combinations of gastrointestinal epithelial permeation barrier enhancers. In other instances, heterogeneous mixtures may contain one low molecular weight heparin and two or more combinations of gastrointestinal epithelial permeation barrier enhancers. In yet other instances, heterogeneous mixtures may contain two or more low molecular weight heparins and a single synergistically effective combination of two or more gastrointestinal epithelial permeation barrier enhancers.

In certain embodiments, oral dosage compositions of the invention may further include one or more pharmaceutically acceptable excipients or oral dosage delivery vehicle as part of a pharmaceutical composition. Excipients may include, but are not limited to, carbohydrates, inorganic salts, antimicrobial agents, antioxidants, surfactants, water, alcohols, polyols, glycerine, vegetable oils, phospholipids, buffers, acids, bases, and any combinations thereof. A carbohydrate such as a sugar, a derivatized sugar such as an alditol, aldonic acid, an esterified sugar, and/or a sugar polymer may also be employed. Some carbohydrate excipients of interest include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. Inorganic salts may include, but are not limited to citric acid, sodium chloride, potassium chloride, sodium sulfate, potassium nitrate, sodium phosphate monobasic, sodium phosphate dibasic, and any combinations thereof.

In certain embodiments, oral dosage compositions of the invention may also include an antimicrobial agent for preventing or deterring microbial growth, such as for example benzalkonium chloride, benzethonium chloride, benzyl alcohol, cetylpyridinium chloride, chlorobutanol, phenol, phenylethyl alcohol, phenylmercuric nitrate, thimersol, and any combinations thereof.

One or more antioxidants may also be employed. Antioxidants, which can reduce or prevent oxidation and thus deterioration of the composition, may include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and any combinations thereof.

One or more surfactants may also be included in compositions of the invention. For example, suitable surfactants may include, but are not limited to polysorbates, such as "Tween 20" and "Tween 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other cations.

Acids or bases may also be present in oral dosage compositions of the invention. For example, acids may include but are not limited to hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and any combinations thereof. Examples of bases include, but are not limited to sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and any combinations thereof.

The amount of any individual excipient in the oral dosage composition will vary depending on the nature and function of the excipient, oral dosage delivery vehicle and particular needs of the composition. In some instances, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the oral dosage composition in an amount of about 1% to about 99% by weight, such as from about 5% to about 98% by weight, such as from about 15 to about 95% by weight of the excipient, including less than 30% by weight. Pharmaceutical excipients along with other excipients that may be employed in compositions of interest are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000, the disclosure of which is herein incorporated by reference.

As described above, compositions of the invention may be administered by any convenient mode of administration so long as the composition is resorbed through the gastrointestinal epithelium (e.g., orally or by nasogastric tube). As such, the formulation may vary. For example, compositions of the invention may be powders or lyophilates that can be reconstituted with a solvent prior to use, dry insoluble compositions for combination with a vehicle prior to use, and emulsions and liquid concentrates for dilution prior to administration. Diluents for reconstituting solid compositions may include, but are not limited to bacteriostatic water for injection, dextrose 5% in water, phosphate buffered saline, Ringer's solution, saline, sterile water, deionized water, and any combinations thereof. In some embodiments, pharmaceutical compositions of the invention may be in the form of a liquid solution or suspension, syrup, tablet, capsule, powder, gel, or any combination thereof for ingestion or application by a nasogastric tube. For example, oral dosage compositions of the invention may be pre-loaded into a tablet, a capsule, caplet device, or the like, depending upon the intended use. In certain embodiments, the compositions are in unit dosage form, such that an amount of the composition is ready in a single oral dose, in a premeasured or pre-packaged form.

Utility

The subject methods and compositions find use in any situation where there is a desire to treat thrombosis or reduce blood coagulation in a subject, a desire to enhance resorption of low molecular weight heparins through the gastrointestinal system and the subject is responsive to treatment with a low molecular weight heparin and a gastrointestinal epithelial barrier permeation enhancer. In certain embodiments, the subject methods and compositions may be employed to treat or prevent a thromboembolic disease in a subject, such as where the thromboembolic disease is associated with myocardial infarction, deep vein thrombosis following surgery, transient ischemic attack, coronary artery bypass graft, peripheral vascular disease, stroke percutaneous transluminal coronary angioplasty, acute promyelocytic leukemia, diabetes, multiple myelomas, septic shock, purpura fulminanas, adult respiratory distress syndrome, angina, insertion and the presence of aortic valve or vascular prosthesis, cardiac catheterization, transluminal endoplasty, heart valve replacement.

The subject methods and compositions also find use in reducing or preventing thrombosis or reducing blood coagulation as prophylaxis in a subject undergoing a surgical or invasive procedure. In particular, the invention provides a method for treating a subject undergoing a surgical or invasive procedure where reduced or elimination of thrombosis would be desirable, by orally administering a therapeutically effective amount of a composition having a low molecular weight heparin and a synergistically effective combination of two or more gastrointestinal epithelial barrier permeation enhancers as detailed herein to the subject.

In certain embodiments, the low molecular weight heparin and subject combination of gastrointestinal epithelial barrier permeation enhancers can be coadministered with one or more different low molecular weight heparins and two or more different gastrointestinal epithelial barrier permeation enhancers, and/or in combination with one or more other therapeutic agents to the subject undergoing a surgical or invasive procedure. Therapeutic agents used to treat a subject undergoing a surgical or invasive procedure can be administered in the same or different compositions and concurrently, before, or after administration of the low molecular weight heparin and the synergistically effective combination of two or more gastrointestinal epithelial barrier permeation enhancers.

Kits

Also provided are kits for use in practicing the subject methods, where the kits may include one or more of the above compositions, e.g., an low molecular weight heparin composition and a synergistically effective combination of two or more gastrointestinal epithelial barrier permeation enhancers, as described above. The kit may further include other components, e.g., administration devices, fluid sources, etc., which may find use in practicing the subject methods. Various components may be packaged as desired, e.g., together or separately. Components of the subject kits may be present in separate containers, or multiple components may be present in a single container, where the containers and/or packaging (or a portion thereof) of the kit may be sterile, as desired.

In addition to above mentioned components, the subject kits may further include instructions for using the components of the kit to practice the subject methods. The instructions for practicing the subject methods are generally recorded on a suitable recording medium. For example, the instructions may be printed, such as on paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. portable flash drive, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXPERIMENTAL

The following examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Bioavailability and Resorption Studies of Low Molecular Weight Heparins in combination with Gastrointestinal Epithelial Barrier Permeation Enhancers The bioavailability of low molecular weight heparins in combination with gastrointestinal epithelial barrier permeation enhancers of interest were studied using the CaCo-2 cell model screening. This method utilizes a human colon carcinoma cell line that expresses a wide range of transporter proteins on its cell membranes. Cell layers are grown on a membrane surface that separates two compartments (24-well plate). An example of the experimental setup for these experiments is illustrated in FIG. 1. Selected low molecular weight heparins and gastrointestinal epithelial barrier permeation enhancer samples were dissolved in RPMI cell medium at a concentration of 1 mg/mL and applied onto the cells in the apical compartment. Cells were incubated at 37° C. in 5% $CO_2$. Medium samples were removed from the basolateral and apical compartment at different time points. The condition of the cell layer was monitored by measurement of the transepithelial electrical resistance (TEER). Samples were analyzed by thrombin generation assay (CAT). Low molecular weight heparin concentration was calculated based on activity from CAT assay.

All low molecular weight heparin and gastrointestinal epithelial barrier permeation enhancer samples were diluted in such a way that the sample concentration was in the range of increasing anticoagulant activity. Based on the initial load concentration values, apical and basolateral concentrations were determined at 2 hour increments (e.g., 2 hours, 4 hours, 6 hours, 8 hours, including 24 hours). Based on the determined basolateral concentrations, the percent resorption was determined for each combination of compounds (I.e., low molecular weight heparin and gastrointestinal epithelial barrier permeation enhancers).

Example 1

An example of the resorption studies described herein is illustrated in Tables 1-3 which summarize the apical and basolateral concentrations of low molecular weight heparin in combination with the gastrointestinal epithelial barrier permeation enhancer, deoxycholine (0.06%) in the Caco-2 cell model. Table 1 illustrates two trials that include starting apical concentrations of the low molecular weight heparin in combination with deoxycholine is about 970 μg/mL (Trial 1) and 1210 μg/mL (Trial 2), respectively. After 8 hours, the apical concentration of the low molecular weight heparin is reduced by about 25% to an average of about 733 μg/mL (Trial 1) and 900 μg/mL (Trial 2).

TABLE 1

| Sample | Start (mg/mL) | 8 hours (mg/mL) |
|---|---|---|
| Trial 1 - LMWH and Deoxycholine 0.06% | | |
| LMWH - Set A | 970 | 740 |
| LMWH - Set B | | 770 |
| LMWH - Set C | | 690 |
| Trial 2 - LMWH and Deoxycholine 0.06% | | |
| LMWH - Set A | 1210 | 880 |
| LMWH - Set B | | 970 |
| LMWH - Set C | | 850 |

Figure 2:
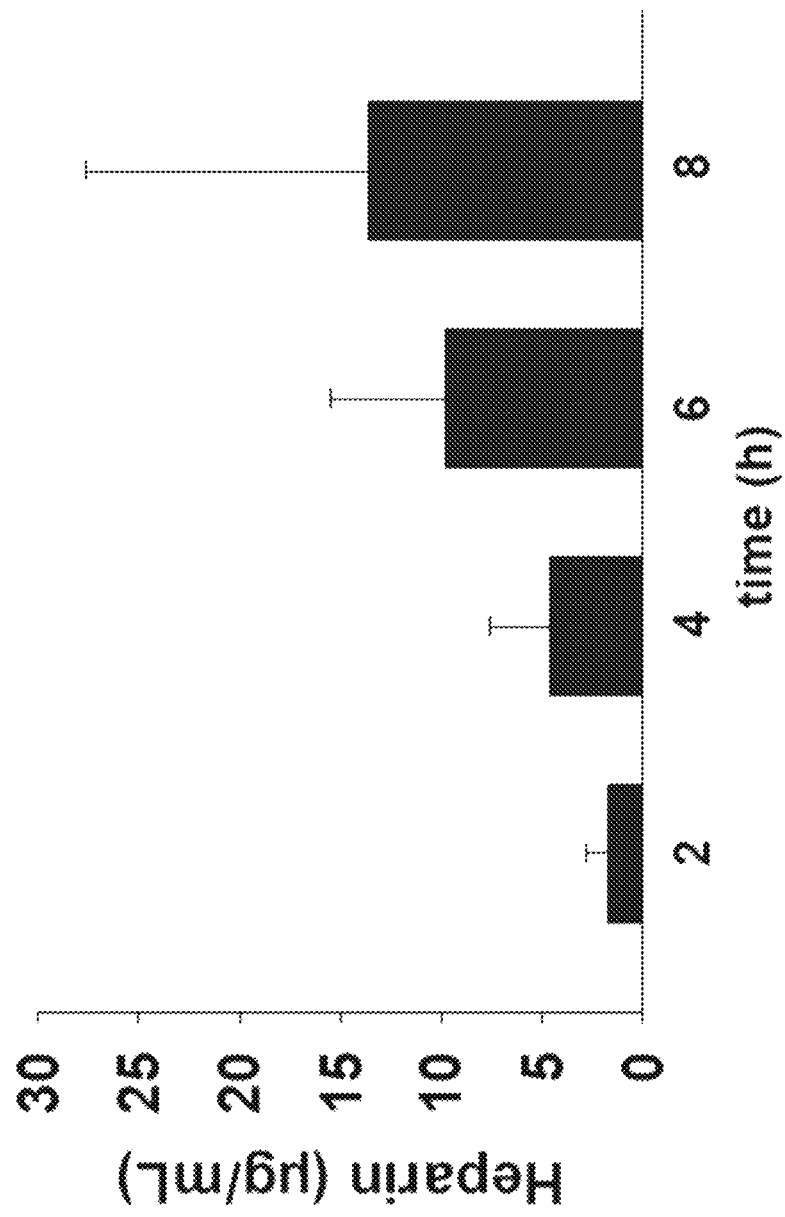
FIG. 2 shows an example of the amount of low molecular weight heparin in combination with the gastrointestinal epithelial barrier permeation enhancer deoxycholine (0.06%) resorbed in CaCo2 bioavailability screening.
Figure 3:
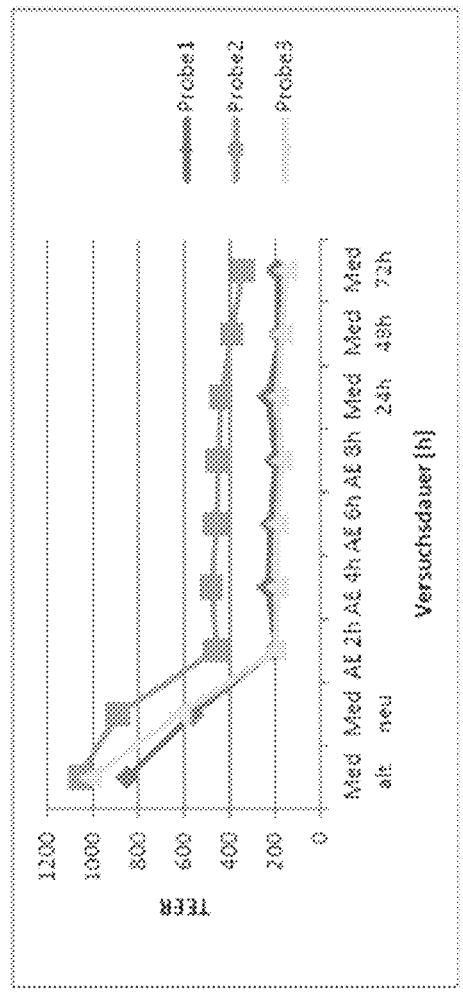
FIG. 3 shows the condition of the cell layer in the CaCo-2 bioavailability screening for low molecular weight heparin in combination with the gastrointestinal epithelial barrier permeation enhancer deoxycholine (0.06%) as measured by transepithelial electrical resistance.

Table 2 illustrates the basolateral concentrations of low molecular weight heparin in combination with deoxycholine (0.08%) of trials 1 and 2 above, at various time points. FIG. 2 shows the basolateral concentrations of low molecular weight heparin in the presence of deoxycholine (0.06%) in the Caco-2 system. FIG. 3 shows the condition of the cell layer as measured by the corresponding transepithelial electrical resistance curves.

TABLE 2

| Sample Concentration (μg/mL) | 2 hours | 4 hours | 6 hours | 8 hours |
|---|---|---|---|---|
| Trial 1 - LMWH and Deoxycholine 0.06% | | | | |
| Dilution Factor | 1 | 0.9 | 0.82 | 0.74 |
| LMWH - Set A | 1.6 | 5.9 | 8.3 | 9.7 |
| LMWH - Set B | 0.6 | 1.3 | 4.7 | 1.9 |
| LMWH - Set C | 2.9 | 6.6 | 16.1 | 29.1 |
| Theoretical Maximum | 190 | 171 | 156 | 141 |
| Trial 2 - LMWH and Deoxycholine 0.06% | | | | |
| Dilution Factor | 1 | 0.9 | 0.82 | 0.74 |
| LMWH - Set A | 4.0 | 11.6 | 15.1 | 16.1 |
| LMWH - Set B | 1.7 | 8.8 | 11.2 | 11.4 |
| LMWH - Set C | 2.4 | 8.7 | 12.9 | 15.1 |
| Theoretical Maximum | 190 | 171 | 156 | 141 |

Table 3 illustrates the percent (%) resorption of low molecular weight heparin in the presence of deoxycholine (0.08%) at various time points.

TABLE 3

| Percent Resorption | 2 hours | 4 hours | 6 hours | 8 hours |
|---|---|---|---|---|
| Trial 1 - LMWH and Deoxycholine 0.06% | | | | |
| Dilution Factor | 1 | 0.9 | 0.82 | 0.74 |
| LMWH - Set A | 0.8 | 3.5 | 5.3 | 6.9 |
| LMWH - Set B | 0.3 | 0.8 | 3.0 | 1.3 |
| LMWH - Set C | 1.5 | 3.9 | 10.3 | 20.6 |
| Trial 2 - LMWH and Deoxycholine 0.06% | | | | |
| Dilution Factor | 1 | 0.9 | 0.82 | 0.74 |
| LMWH - Set A | 2.1 | 6.8 | 9.7 | 11.4 |
| LMWH - Set B | 0.9 | 5.1 | 7.2 | 8.1 |
| LMWH - Set C | 1.3 | 5.1 | 8.3 | 10.7 |

Example 2

Another example of the resorption studies described herein is illustrated in Tables 4-6 which summarize the apical and basolateral concentrations of low molecular weight heparin in combination with the gastrointestinal epithelial barrier permeation enhancer, deoxycholine (0.08%) in the Caco-2 cell model. Table 4 illustrates two trials that include starting apical concentrations of the low molecular weight heparin in combination with deoxycholine is about 930 μg/mL (Trial 1) and 1360 μg/mL (Trial 2), respectively. After 8 hours, the apical concentration of the low molecular weight heparin is reduced by about 45% to an average of about 560 μg/mL (Trial 1) and 683 μg/mL (Trial 2).

TABLE 4

| Sample | Start (mg/mL) | 8 hours (mg/mL) |
|---|---|---|
| Trial 1 - LMWH and Deoxycholine 0.08% | | |
| LMWH - Set A | 930 | 610 |
| LMWH - Set B | | 520 |

TABLE 4-continued

| Sample | Start (mg/mL) | 8 hours (mg/mL) |
|---|---|---|
| LMWH - Set C | | 550 |
| Trial 2 - LMWH and Deoxycholine 0.06% | | |
| LMWH - Set A | 1360 | 630 |
| LMWH - Set B | | 710 |
| LMWH - Set C | | 710 |

Figure 4:
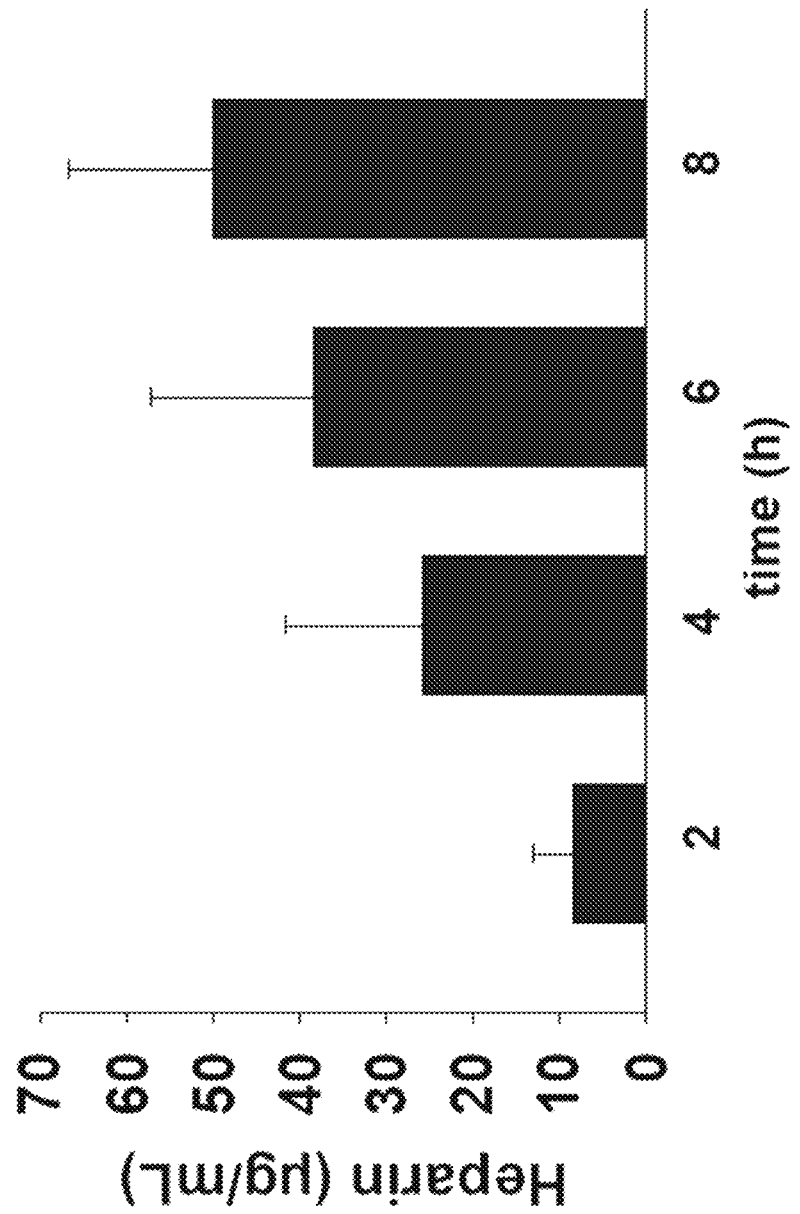
FIG. 4 shows an example of the amount of low molecular weight heparin in combination with the gastrointestinal epithelial barrier permeation enhancer deoxycholine (0.08%) resorbed in CaCo2 bioavailability screening.
Figure 5:
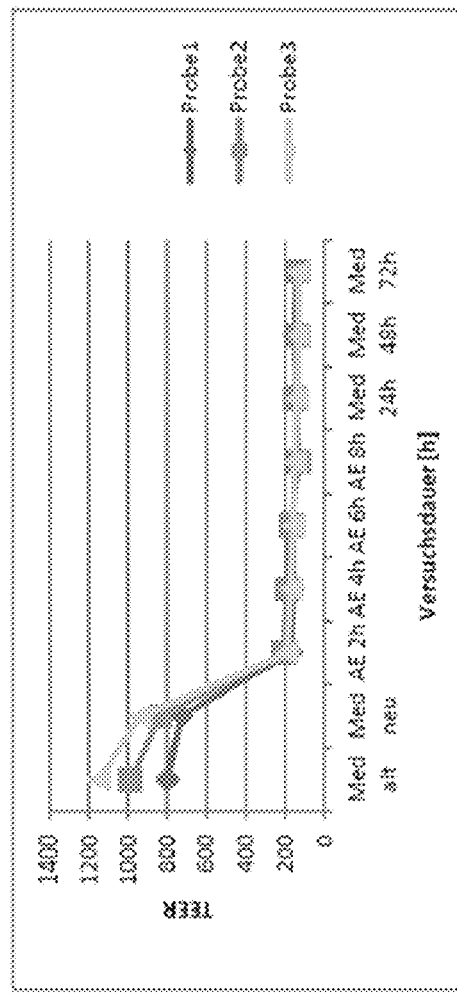
FIG. 5 shows the condition of the cell layer in the CaCo-2 bioavailability screening for low molecular weight heparin in combination with the gastrointestinal epithelial barrier permeation enhancer deoxycholine (0.08%) as measured by transepithelial electrical resistance.

Table 5 illustrates the basolateral concentrations of low molecular weight heparin in combination with deoxycholine (0.08%) of trials 1 and 2 above, at various time points. FIG. 4 shows the basolateral concentrations of low molecular weight heparin in the presence of deoxycholine (0.08%) in the Caco-2 system. FIG. 5 shows the condition of the cell layer as measured by the corresponding transepithelial electrical resistance curves.

TABLE 5

| Sample Concentration (µg/mL) | 2 hours | 4 hours | 6 hours | 8 hours |
|---|---|---|---|---|
| Trial 1 - LMWH and Deoxycholine 0.08% | | | | |
| Dilution Factor | 1 | 0.9 | 0.82 | 0.74 |
| LMWH - Set A | 13.3 | 41.8 | 51.8 | 61.8 |
| LMWH - Set B | 4.0 | 9.9 | 17.2 | 30.7 |
| LMWH - Set C | 7.8 | 25.7 | 46.5 | 57.2 |
| Theoretical Maximum | 190 | 171 | 156 | 141 |
| Trial 2 - LMWH and Deoxycholine 0.08% | | | | |
| Dilution Factor | 1 | 0.9 | 0.82 | 0.74 |
| LMWH - Set A | 18.0 | 54.0 | 79.3 | 97.1 |
| LMWH - Set B | 10.6 | 49.5 | 69.5 | 93.3 |
| LMWH - Set C | 10.8 | 42.9 | 61.0 | 77.1 |
| Theoretical Maximum | 190 | 171 | 156 | 141 |

Table 6 illustrates the percent (%) resorption of low molecular weight heparin in the presence of deoxycholine (0.08%) at various time points.

TABLE 6

| Percent Resorption | 2 hours | 4 hours | 6 hours | 8 hours |
|---|---|---|---|---|
| Trial 1 - LMWH and Deoxycholine 0.08% | | | | |
| Dilution Factor | 1 | 0.9 | 0.82 | 0.74 |
| LMWH - Set A | 7.0 | 24.4 | 33.2 | 43.8 |
| LMWH - Set B | 2.1 | 5.8 | 11.0 | 21.8 |
| LMWH - Set C | 4.1 | 15.0 | 29.8 | 40.6 |
| Trial 2 - LMWH and Deoxycholine 0.08% | | | | |
| Dilution Factor | 1 | 0.9 | 0.82 | 0.74 |
| LMWH - Set A | 9.4 | 31.6 | 50.8 | 68.9 |
| LMWH - Set B | 5.6 | 29.1 | 44.6 | 66.2 |
| LMWH - Set C | 5.7 | 25.1 | 39.1 | 54.7 |

Example 3

Another example of the resorption studies described herein is illustrated in Tables 7-9 which summarize the apical and basolateral concentrations of low molecular weight heparin in combination with the gastrointestinal epithelial barrier permeation enhancer, chitosan (3% w/v) in the Caco-2 cell model. Table 7 illustrates two trials that include starting apical concentrations of the low molecular weight heparin in combination with chitosan is about 910 µg/mL (Trial 1) and 1390 µg/mL (Trial 2), respectively. After 8 hours, the apical concentration of the low molecular weight heparin is reduced by about 35% to an average of about 663 µg/mL (Trial 1) and 886 µg/mL (Trial 2).

TABLE 7

| Sample | Start (mg/mL) | 8 hours (mg/mL) |
|---|---|---|
| Trial 1 - LMWH and Chitosan (3% w/v) | | |
| LMWH - Set A | 910 | 720 |
| LMWH - Set B | | 600 |
| LMWH - Set C | | 670 |
| Trial 2 - LMWH and Chitosan (3% w/v) | | |
| LMWH - Set A | 1390 | 860 |
| LMWH - Set B | | 870 |
| LMWH - Set C | | 930 |

Figure 6:
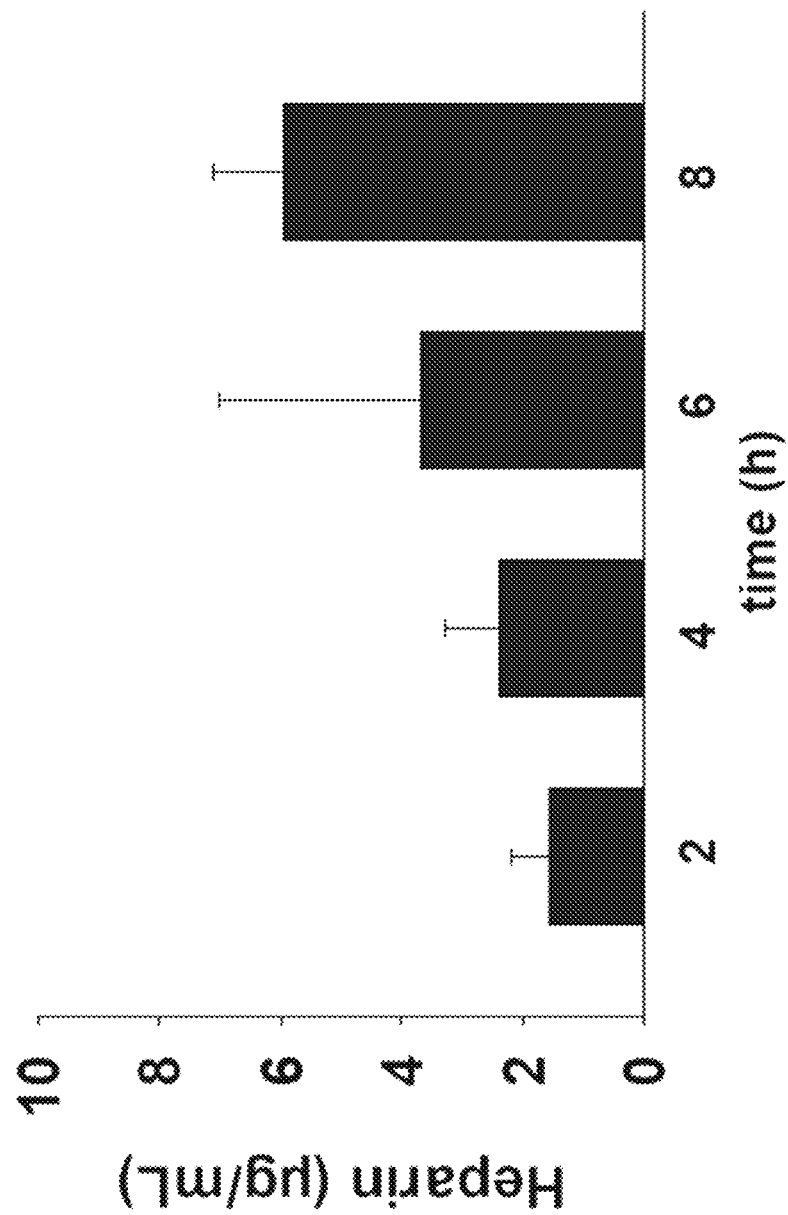
FIG. 6 shows an example of the amount of low molecular weight heparin in combination with the gastrointestinal epithelial barrier permeation enhancer chitosan (3% w/v) resorbed in CaCo2 bioavailability screening.
Figure 7:
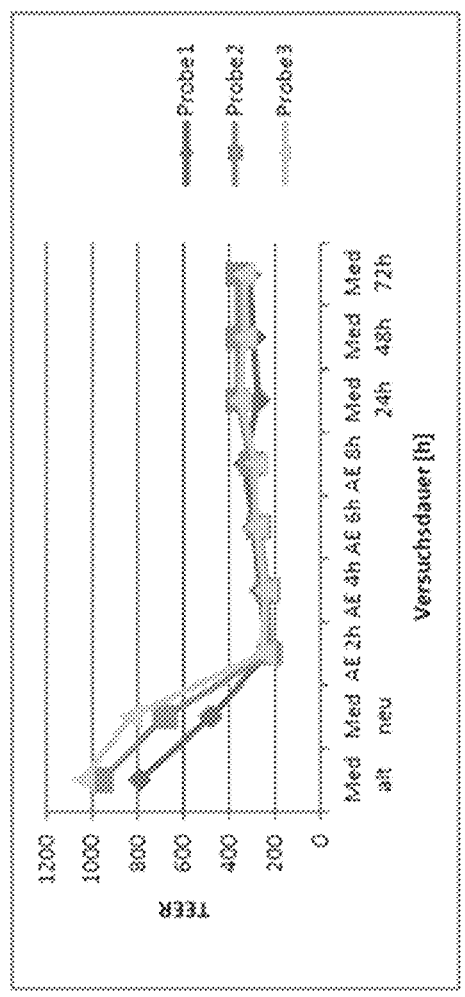
FIG. 7 shows the condition of the cell layer in the CaCo-2 bioavailability screening for low molecular weight heparin in combination with the gastrointestinal epithelial barrier permeation enhancer chitosan (3% w/v) as measured by transepithelial electrical resistance.

Table 8 illustrates the basolateral concentrations of low molecular weight heparin in combination with chitosan of trials 1 and 2 above, at various time points. FIG. 6 shows the basolateral concentrations of low molecular weight heparin in the presence of chitosan (3% w/v) in the Caco-2 system. FIG. 7 shows the condition of the cell layer as measured by the corresponding transepithelial electrical resistance curves.

TABLE 8

| Sample Concentration (µg/mL) | 2 hours | 4 hours | 6 hours | 8 hours |
|---|---|---|---|---|
| Trial 1 - LMWH and Chitosan 3% w/v | | | | |
| Dilution Factor | 1 | 0.9 | 0.82 | 0.74 |
| LMWH - Set A | 2.2 | 3.4 | 2.0 | 7.1 |
| LMWH - Set B | 1.5 | 1.9 | 7.5 | 6.0 |
| LMWH - Set C | 1.0 | 1.8 | 1.6 | 4.8 |
| Theoretical Maximum | 190 | 171 | 156 | 141 |
| Trial 2 - LMWH and Chitosan 3% w/v | | | | |
| Dilution Factor | 1 | 0.9 | 0.82 | 0.74 |
| LMWH - Set A | 0.2 | 3.4 | 3.8 | 4.2 |
| LMWH - Set B | 2.9 | 5.4 | 4.6 | 7.5 |
| LMWH - Set C | 1.1 | 6.2 | 6.7 | 7.7 |
| Theoretical Maximum | 190 | 171 | 156 | 141 |

Table 9 illustrates the percent (%) resorption of low molecular weight heparin in the presence of chitosan (3% w/v) at various time points.

TABLE 9

| Percent Resorption | 2 hours | 4 hours | 6 hours | 8 hours |
|---|---|---|---|---|
| Trial 1 - LMWH and Chitosan 3% w/v | | | | |
| Dilution Factor | 1 | 0.9 | 0.82 | 0.74 |
| LMWH - Set A | 1.2 | 2.0 | 1.3 | 5.0 |
| LMWH - Set B | 0.8 | 1.1 | 4.8 | 4.3 |
| LMWH - Set C | 0.5 | 1.1 | 1.0 | 3.4 |
| Trial 2 - LMWH and Chitosan 3% w/v | | | | |
| Dilution Factor | 1 | 0.9 | 0.82 | 0.74 |
| LMWH - Set A | 0.1 | 2.0 | 2.4 | 3.0 |
| LMWH - Set B | 1.5 | 3.2 | 3.0 | 5.3 |
| LMWH - Set C | 0.6 | 3.6 | 4.3 | 5.5 |

Example 4

Another example of the resorption studies described herein is illustrated in Tables 10-12 which summarize the apical and basolateral concentrations of low molecular weight heparin in combination with the gastrointestinal epithelial barrier permeation enhancer, bromelain (0.5 mg/mL) in the Caco-2 cell model. Table 10 illustrates two trials that include starting apical concentrations of the low molecular weight heparin in combination with bromelain is about 1060 µg/mL (Trial 1) and 1230 µg/mL (Trial 2), respectively. After 8 hours, the apical concentration of the low molecular weight heparin is reduced by about 25% to an average of about 870 µg/mL (Trial 1) and 890 µg/mL (Trial 2).

TABLE 10

| Sample | Start (mg/mL) | 8 hours (mg/mL) |
|---|---|---|
| Trial 1 - LMWH and Bromelain (0.5 mg/mL) | | |
| LMWH - Set A | 1060 | 830 |
| LMWH - Set B | | 990 |
| LMWH - Set C | | 790 |
| Trial 2 - LMWH and Bromelain (0.5 mg/mL) | | |
| LMWH - Set A | 1230 | 950 |
| LMWH - Set B | | 990 |
| LMWH - Set C | | 730 |

Figure 8:
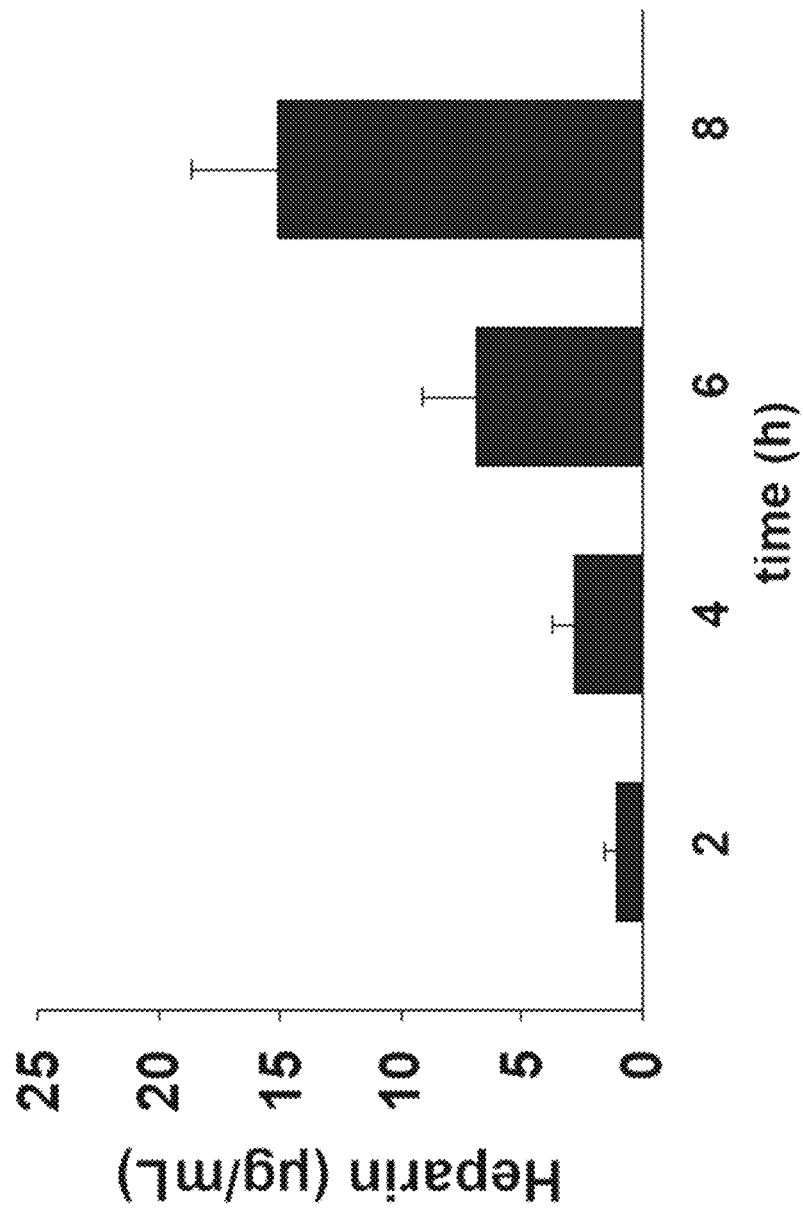
FIG. 8 shows an example of the amount of low molecular weight heparin in combination with the gastrointestinal epithelial barrier permeation enhancer bromelain (0.5 mg/mL) resorbed in CaCo2 bioavailability screening.
Figure 9:
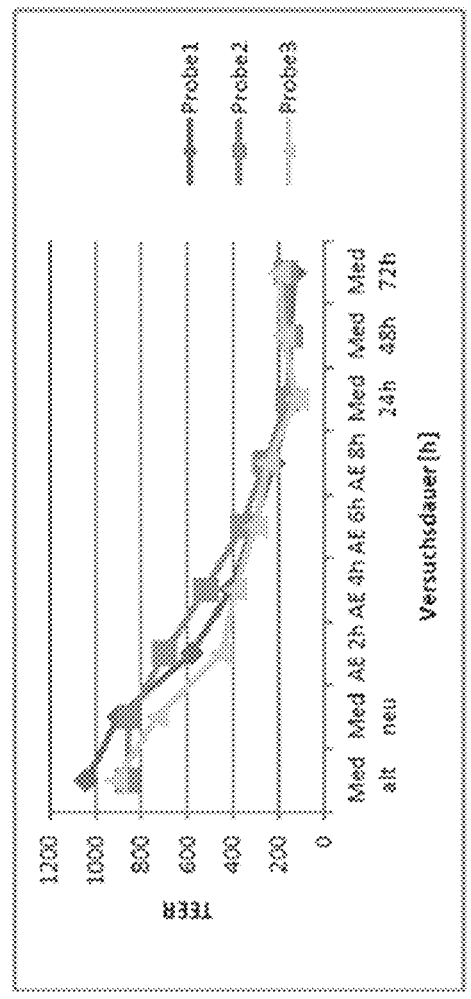
FIG. 9 shows the condition of the cell layer in the CaCo-2 bioavailability screening for low molecular weight heparin in combination with the gastrointestinal epithelial barrier permeation enhancer bromelain (0.5 mg/mL) as measured by transepithelial electrical resistance.

Table 11 illustrates the basolateral concentrations of low molecular weight heparin in combination with bromelain of trials 1 and 2 above, at various time points. FIG. 8 shows the basolateral concentrations of low molecular weight heparin in the presence of bromelain in the Caco-2 system. FIG. 9 shows the condition of the cell layer as measured by the corresponding transepithelial electrical resistance curves.

TABLE 11

| Sample Concentration (µg/mL) | 2 hours | 4 hours | 6 hours | 8 hours |
|---|---|---|---|---|
| Trial 1 - LMWH and Bromelain (0.5 mg/mL) | | | | |
| Dilution Factor | 1 | 0.9 | 0.82 | 0.74 |
| LMWH - Set A | 1.4 | 3.6 | 4.5 | 18.5 |
| LMWH - Set B | 0.5 | 1.7 | 7.1 | 14.2 |
| LMWH - Set C | 1.2 | 2.9 | 8.9 | 11.0 |
| Theoretical Maximum | 190 | 171 | 156 | 141 |
| Trial 2 - LMWH and Bromelain (0.5 mg/mL) | | | | |
| Dilution Factor | 1 | 0.9 | 0.82 | 0.74 |
| LMWH - Set A | 0.4 | 1.9 | 16.6 | 20.8 |
| LMWH - Set B | 1.5 | 5.5 | 14.0 | 21.0 |
| LMWH - Set C | 0.3 | 12.2 | 17.9 | 21.4 |
| Theoretical Maximum | 190 | 171 | 156 | 141 |

Table 12 illustrates the percent (%) resorption of low molecular weight heparin in the presence of bromelain (0.5 mg/mL) at various time points.

TABLE 12

| Percent Resorption | 2 hours | 4 hours | 6 hours | 8 hours |
|---|---|---|---|---|
| Trial 1 - LMWH and Bromelain (0.5 mg/mL) | | | | |
| Dilution Factor | 1 | 0.9 | 0.82 | 0.74 |
| LMWH - Set A | 0.7 | 2.1 | 2.9 | 13.1 |
| LMWH - Set B | 0.3 | 1.0 | 4.6 | 10.0 |
| LMWH - Set C | 0.6 | 1.7 | 5.7 | 7.8 |
| Trial 2 - LMWH and Bromelain (0.5 mg/mL) | | | | |
| Dilution Factor | 1 | 0.9 | 0.82 | 0.74 |
| LMWH - Set A | 0.2 | 1.1 | 10.6 | 14.8 |
| LMWH - Set B | 0.8 | 3.2 | 9.0 | 14.9 |
| LMWH - Set C | 0.2 | 7.1 | 11.5 | 15.2 |

Example 5

Another example of the resorption studies described herein is illustrated in Tables 13-15 which summarize the apical and basolateral concentrations of low molecular weight heparin in combination with the gastrointestinal epithelial barrier permeation enhancer, sodium caprate (12 mM) in the Caco-2 cell model. Table 13 illustrates two trials that include starting apical concentrations of the low molecular weight heparin in combination with sodium caprate is about 920 µg/mL (Trial 1) and 1150 µg/mL (Trial 2), respectively. After 8 hours, the apical concentration of the low molecular weight heparin is reduced by about 20% to an average of about 803 µg/mL (Trial 1) and 840 µg/mL (Trial 2).

TABLE 13

| Sample | Start (mg/mL) | 8 hours (mg/mL) |
|---|---|---|
| Trial 1 - LMWH and Sodium Caprate (12 mM) | | |
| LMWH - Set A | 920 | 810 |
| LMWH - Set B | | 830 |
| LMWH - Set C | | 770 |
| Trial 2 - LMWH and Sodium Caprate (12 mM) | | |
| LMWH - Set A | 1150 | 730 |
| LMWH - Set B | | 880 |
| LMWH - Set C | | 910 |

Figure 10:
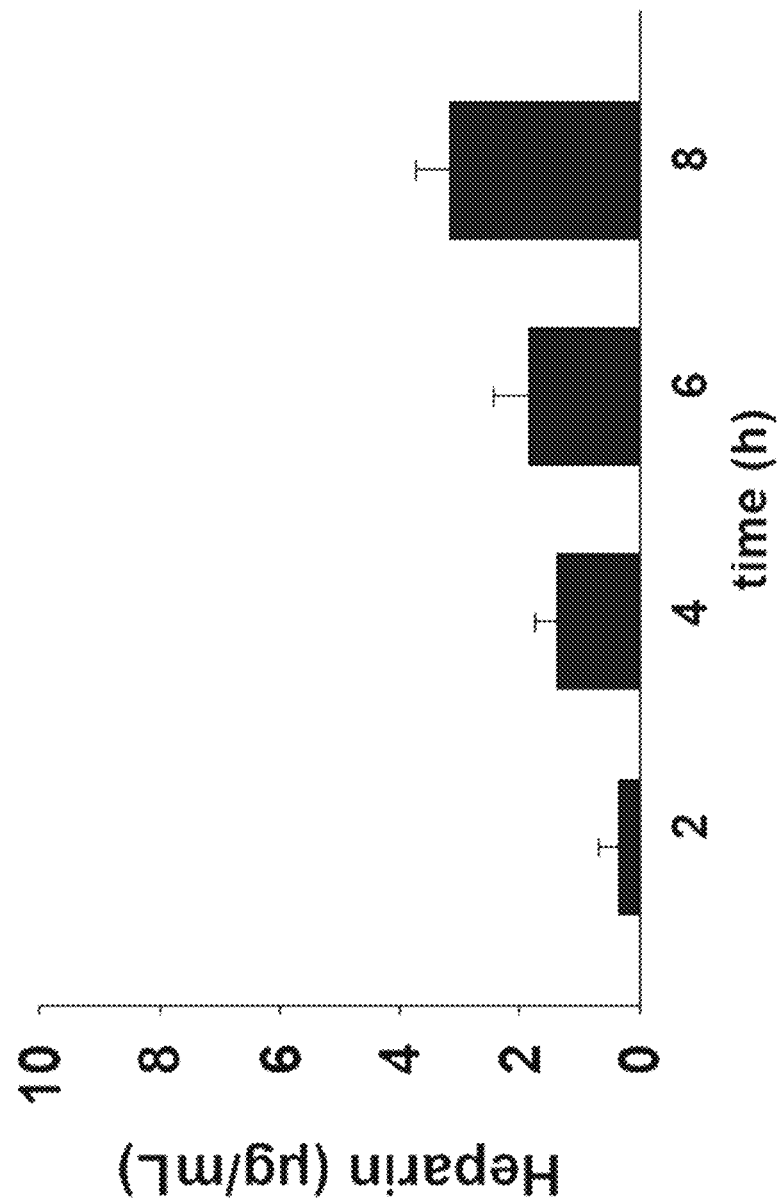
FIG. 10 shows an example of the amount of low molecular weight heparin in combination with the gastrointestinal epithelial barrier permeation enhancer sodium caprate (12 mM) resorbed in CaCo2 bioavailability screening.
Figure 11:
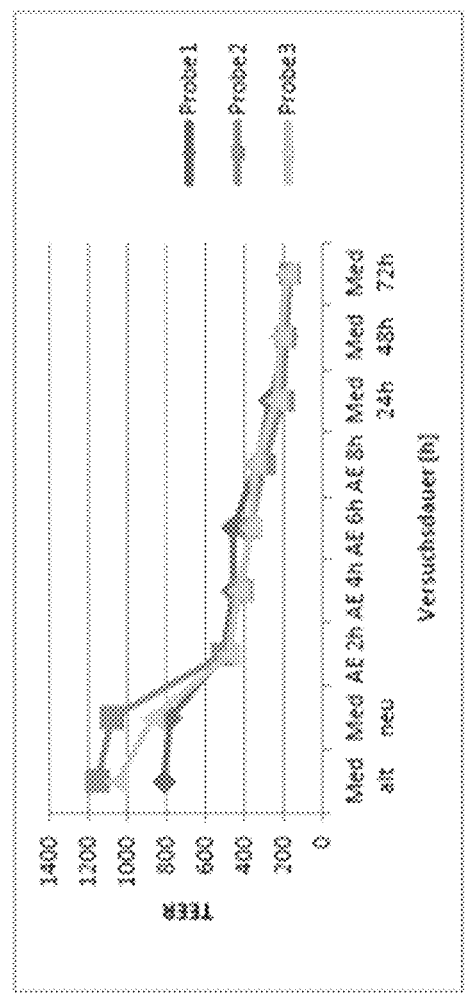
FIG. 11 shows the condition of the cell layer in the CaCo-2 bioavailability screening for low molecular weight heparin in combination with the gastrointestinal epithelial barrier permeation enhancer sodium caprate (12 mM) as measured by transepithelial electrical resistance.

Table 14 illustrates the basolateral concentrations of low molecular weight heparin in combination with sodium caprate of trials 1 and 2 above, at various time points. FIG. 10 shows the basolateral concentrations of low molecular weight heparin in the presence of sodium caprate in the Caco-2 system. FIG. 11 shows the condition of the cell layer as measured by the corresponding transepithelial electrical resistance curves.

TABLE 14

| Sample Concentration (µg/mL) | 2 hours | 4 hours | 6 hours | 8 hours |
|---|---|---|---|---|
| Trial 1 - LMWH and Sodium Caprate (12 mM) | | | | |
| Dilution Factor | 1 | 0.9 | 0.82 | 0.74 |
| LMWH - Set A | 0.7 | 1.1 | 1.4 | 2.5 |
| LMWH - Set B | 0 | 1.3 | 1.6 | 3.3 |
| LMWH - Set C | 0.4 | 1.8 | 2.5 | 3.7 |
| Theoretical Maximum | 190 | 171 | 156 | 141 |
| Trial 2 - LMWH and Sodium Caprate (12 mM) | | | | |
| Dilution Factor | 1 | 0.9 | 0.82 | 0.74 |
| LMWH - Set A | 0.2 | 1.7 | 3.2 | 4.7 |
| LMWH - Set B | 0.3 | 2.4 | 2.8 | 3.1 |
| LMWH - Set C | 0 | 4.5 | 4.8 | 7.5 |
| Theoretical Maximum | 190 | 171 | 156 | 141 |

Table 15 illustrates the percent (%) resorption of low molecular weight heparin in the presence of sodium caprate (12 mM) at various time points.

TABLE 15

| Percent Resorption | 2 hours | 4 hours | 6 hours | 8 hours |
|---|---|---|---|---|
| Trial 1 - LMWH and Sodium Caprate (12 mM) | | | | |
| Dilution Factor | 1 | 0.9 | 0.82 | 0.74 |
| LMWH - Set A | 0.4 | 0.6 | 0.9 | 1.8 |
| LMWH - Set B | 0 | 0.8 | 1.0 | 2.3 |
| LMWH - Set C | 0.2 | 1.1 | 1.6 | 2.6 |

TABLE 15-continued

| Percent Resorption | 2 hours | 4 hours | 6 hours | 8 hours |
|---|---|---|---|---|
| Trial 2 - LMWH and Sodium Caprate (12 mM) | | | | |
| Dilution Factor | 1 | 0.9 | 0.82 | 0.74 |
| LMWH - Set A | 0.1 | 1.0 | 2.1 | 3.3 |
| LMWH - Set B | 0.2 | 1.4 | 1.8 | 2.2 |
| LMWH - Set C | 0 | 2.6 | 3.1 | 5.3 |

Example 6

Another example of the resorption studies described herein is illustrated in Tables 16-18 which summarize the apical and basolateral concentrations of low molecular weight heparin with the synergistically effective combination of gastrointestinal epithelial barrier permeation enhancers, chitosan (3% w/v) and bromelain (0.5 mg/mL) in the Caco-2 cell model. Table 16 illustrates two trials that include starting apical concentrations of the low molecular weight heparin in combination with the synergistically effective combination of chitosan (3% w/v) and bromelain (0.5 mg/mL) is about 920 µg/mL (Trial 1) and 1250 µg/mL (Trial 2), respectively. After 8 hours, the apical concentration of the low molecular weight heparin is reduced by about 55% to an average of about 493 µg/mL (Trial 1) and 560 µg/mL (Trial 2).

TABLE 16

| Sample | Start (mg/mL) | 8 hours (mg/mL) |
|---|---|---|
| Trial 1 - LMWH and Chitosan (3% w/v) and Bromelain (0.5 mg/mL) | | |
| LMWH - Set A | 920 | 550 |
| LMWH - Set B | | 450 |
| LMWH - Set C | | 480 |
| Trial 2 - LMWH and Chitosan (3% w/v) and Bromelain (0.5 mg/mL) | | |
| LMWH - Set A | 1250 | 600 |
| LMWH - Set B | | 470 |
| LMWH - Set C | | 610 |

Figure 12:
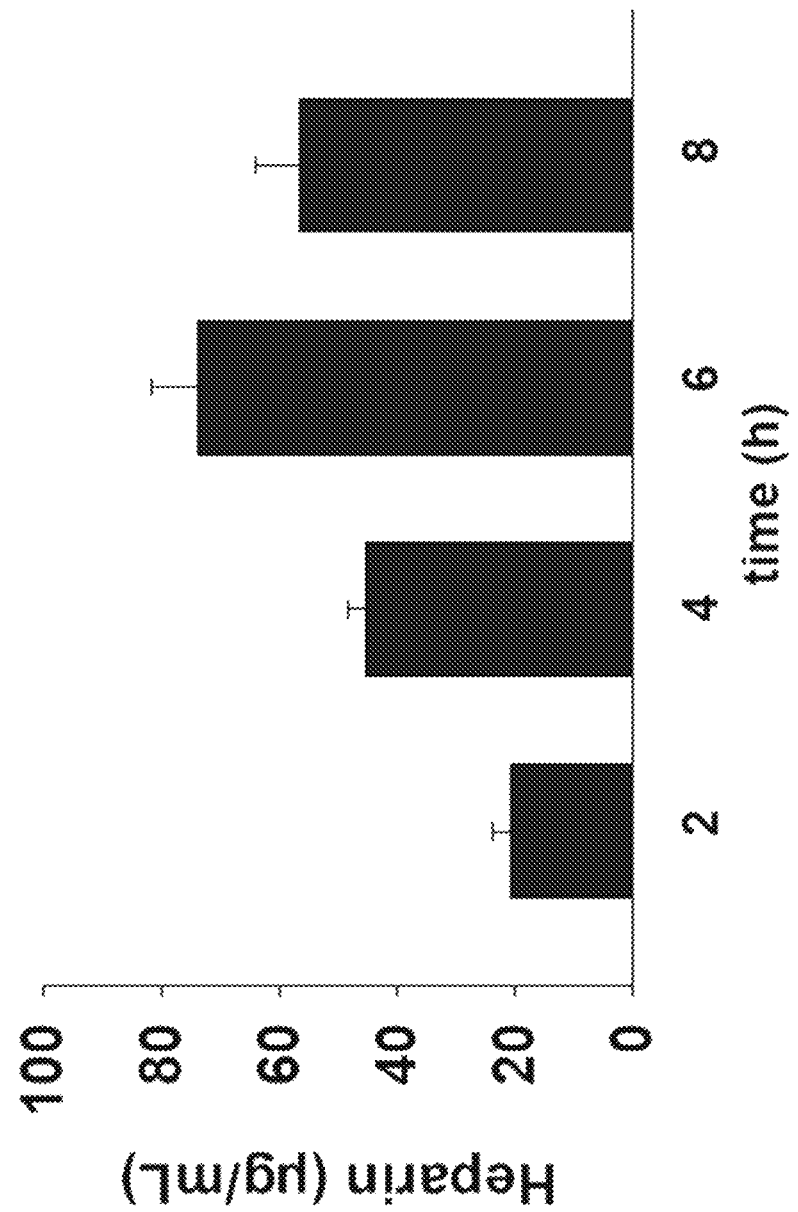
FIG. 12 shows an example of the amount of low molecular weight heparin with a synergistically effective combination of the gastrointestinal epithelial barrier permeation enhancers chitosan (3% w/v) and bromelain (0.5 mg/mL) resorbed in CaCo2 bioavailability screening.
Figure 13:
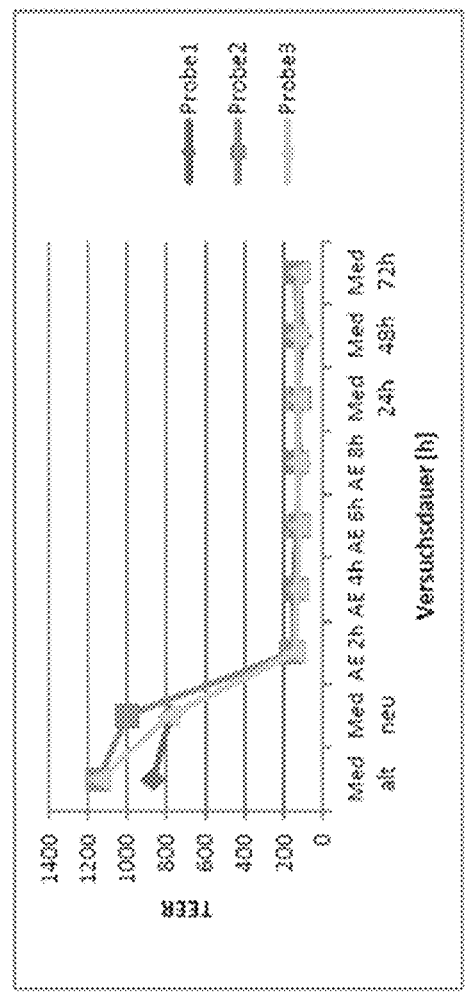
FIG. 13 shows the condition of the cell layer in the CaCo-2 bioavailability screening for low molecular weight heparin with a synergistically effective combination of the gastrointestinal epithelial barrier permeation enhancers chitosan (3% w/v) and bromelain (0.5 mg/mL) as measured by transepithelial electrical resistance.

Table 17 illustrates the basolateral concentrations of low molecular weight heparin and a synergistically effective combination of unmodified chitosan and bromelain of trials 1 and 2 above, at various time points. FIG. 12 shows the basolateral concentrations of low molecular weight heparin in the presence of a synergistically effective combination of chitosan and bromelain in the Caco-2 system. FIG. 13 shows the condition of the cell layer as measured by the corresponding transepithelial electrical resistance curves.

TABLE 17

| Sample Concentration (µg/mL) | 2 hours | 4 hours | 6 hours | 8 hours |
|---|---|---|---|---|
| Trial 1 - LMWH and Chitosan (3% w/v) and Bromelain (0.5 mg/mL) | | | | |
| Dilution Factor | 1 | 0.9 | 0.82 | 0.74 |
| LMWH - Set A | 17.2 | 43.8 | 72.2 | 64.9 |
| LMWH - Set B | 20.8 | 43.3 | 67.6 | 51.1 |
| LMWH - Set C | 23.5 | 48.8 | 82.3 | 54.2 |
| Theoretical Maximum | 190 | 171 | 156 | 141 |
| Trial 2 - LMWH and Chitosan (3% w/v) and Bromelain (0.5 mg/mL) | | | | |
| Dilution Factor | 1 | 0.9 | 0.82 | 0.74 |
| LMWH - Set A | 18.4 | 71.2 | 90.8 | 68.6 |
| LMWH - Set B | 26.9 | 83.5 | 96.9 | 84.8 |
| LMWH - Set C | 32.2 | 77.1 | 104.8 | 90.0 |
| Theoretical Maximum | 190 | 171 | 156 | 141 |

Table 18 illustrates the percent (%) resorption of low molecular weight heparin in the presence of a synergistically effective combination of unmodified chitosan and bromelain at various time points.

TABLE 18

| Percent Resorption | 2 hours | 4 hours | 6 hours | 8 hours |
|---|---|---|---|---|
| Trial 1 - LMWH and Chitosan (3% w/v) and Bromelain (0.5 mg/mL) | | | | |
| Dilution Factor | 1 | 0.9 | 0.82 | 0.74 |
| LMWH - Set A | 9.1 | 25.6 | 46.3 | 46.0 |
| LMWH - Set B | 10.9 | 25.3 | 43.3 | 36.2 |
| LMWH - Set C | 12.4 | 28.5 | 52.8 | 38.4 |
| Trial 2 - LMWH and Chitosan (3% w/v) and Bromelain (0.5 mg/mL) | | | | |
| Dilution Factor | 1 | 0.9 | 0.82 | 0.74 |
| LMWH - Set A | 9.6 | 41.6 | 58.2 | 48.7 |
| LMWH - Set B | 5.6 | 48.8 | 62.1 | 60.1 |
| LMWH - Set C | 16.9 | 45.1 | 67.2 | 63.8 |

Table 19 is a summary of percent resorption of low molecular weight heparins in the Caco-2 cell model in the presence of several gastrointestinal epithelial permeation enhancers at various concentrations. As shown in Table 19, the synergistically effective combination of chitosan (3% w/v) and bromelain (0.5 mg/mL) demonstrated greater resorption of low molecular weight heparin than the additive sum of chitosan (3% w/v) alone plus bromelain (0.5 mg/mL) alone.

TABLE 19

| Average Percent Resorption at 8 hours | Low Molecular Weight Heparin |
|---|---|
| Molecular Weight | 3 kD |
| No enhancer | 1.0 |
| Sodium Caprate - 12 mM | 2.9 |
| Deoxycholate - 0.06% | 9.8 |
| Deoxycholate - 0.08% | 49.3 |
| Bromelain - 0.5 mg/mL | 12.8 |
| Chitosan - 3% | 4.4 |
| Bromelain/Chitosan - 0.5 mg/mL: 3% | 48.9 |

Figure 14:
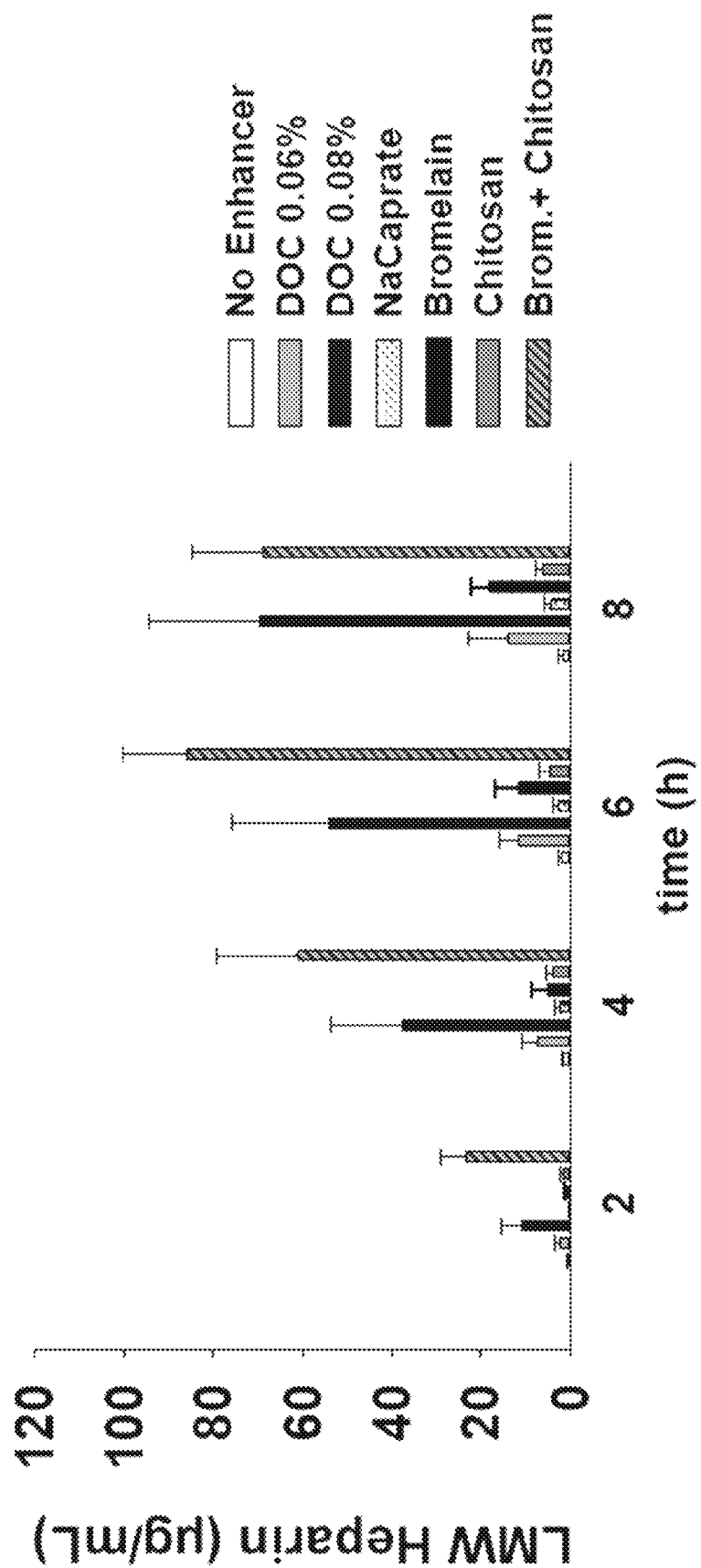
FIG. 14 show an example of resorption data acquired in the CaCo-2 bioavailability screening for low molecular weight heparin in combination with various gastrointestinal epithelial barrier permeation enhancers.

FIG. 14 illustrates low molecular weight heparin resorption in Caco-2 cell models: 1) in the absence of any gastrointestinal epithelial barrier permeation enhancers; 2) in the presence of different individual gastrointestinal epithelial barrier permeation enhancers (e.g., sodium caprate, deoxycholate, bromelain, chitosan); and 3) in the presence of a synergistically effective combination of bromelain and chitosan at different times (i.e., 2 hours, 4 hours, 6 hours and 8 hours). As illustrated in FIG. 14, the synergistically effective combination of chitosan (3% w/v) and bromelain (0.5 mg/mL) demonstrated greater resorption of low molecular weight heparin than the additive sum of chitosan (3% w/v) alone plus bromelain (0.5 mg/mL) alone.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended claims.

What is claimed is:

1. An oral dosage composition comprising:
a low-molecular weight heparin;
a synergistically effective combination of two gastrointestinal epithelial barrier permeation enhancers that increases permeation of the low molecular weight heparin by an amount that is greater than the sum of the increase in permeation of the low molecular weight heparin with each individual gastrointestinal epithelial barrier permeation enhancer; and
an oral dosage delivery vehicle,
wherein said permeation enhancers comprise bromelain and chitosan.

2. The oral dosage composition according to claim 1, wherein the combination of two gastrointestinal epithelial barrier permeation enhancers improves gastrointestinal epithelial barrier permeation of the low-molecular weight heparin by 3-fold or greater than is achieved by the additive sum of each gastrointestinal epithelial barrier permeation enhancer.

3. The oral dosage composition according to claim 1, wherein the chitosan is carboxymethyl chitosan.

4. The oral dosage composition according to claim 3, wherein the combination of two or more gastrointestinal epithelial barrier permeation enhancers comprises carboxymethyl chitosan and bromelain.

5. The oral dosage composition according to claim 4, wherein carboxymethyl chitosan and bromelain are present in a ratio sufficient to provide a 3-fold or greater gastrointestinal epithelial barrier permeation enhancement than is achieved by the additive sum of carboxymethyl chitosan and bromelain.

6. The oral dosage composition according to claim 4, wherein the combination of two or more gastrointestinal epithelial barrier permeation enhancers comprises about 0.75% w/v to about 3% w/v carboxymethyl chitosan and about 0.125 mg/mL to about 0.5 mg/mL bromelain.

7. The oral dosage composition according to claim 4, wherein the combination of two or more gastrointestinal epithelial barrier permeation enhancers comprises about 1.5% w/v carboxymethyl chitosan and about 0.25 mg/mL bromelain.

8. The oral dosage composition according to claim 1, wherein the chitosan is unmodified chitosan.

9. The oral dosage composition according to claim 8, wherein the chitosan is unthiolated chitosan.

10. The oral dosage composition according to claim 8, wherein the combination of two or more gastrointestinal epithelial barrier permeation enhancers comprises unmodified chitosan and bromelain.

11. An oral dosage composition comprising:
a low-molecular weight heparin;
a synergistically effective combination of unmodified chitosan and bromelain in an amount sufficient to provide gastrointestinal epithelial barrier permeation enhancement that is greater than is achieved by the additive sum of unmodified chitosan and bromelain individually; and
an oral dosage delivery vehicle.

12. A method comprising:
orally administering to a subject an oral dosage composition comprising:
a low-molecular weight heparin;
a synergistically effective combination of two gastrointestinal epithelial barrier permeation enhancers that increases permeation of the low molecular weight heparin by an amount that is greater than the sum of the increase in permeation of the low molecular weight heparin with each individual gastrointestinal epithelial barrier permeation enhancer; and
an oral dosage delivery vehicle,
wherein said permeation enhancers comprise bromelain and chitosan.

13. The method according to claim 12, wherein the combination of two gastrointestinal epithelial barrier permeation enhancers improves gastrointestinal epithelial barrier permeation of the low-molecular weight heparin by 3-fold or greater than is achieved by the additive sum of each gastrointestinal epithelial barrier permeation enhancer.

* * * * *